(12) United States Patent
Halpern et al.

(10) Patent No.: US 12,153,044 B2
(45) Date of Patent: Nov. 26, 2024

(54) 2-DIMENSIONAL SURFACES CAPABLE OF MONITORING STIMULI-RESPONSIVE BEHAVIOR AND METHODS OF USE THEREOF

(71) Applicants: University of New Hampshire, Durham, NH (US); University of New England, Biddeford, ME (US)

(72) Inventors: Jeffrey M. Halpern, Durham, NH (US); Eva Rose M. Balog, Biddeford, ME (US)

(73) Assignees: University of New England, Biddeford, ME (US); University of New Hampshire, Durham, NH (US)

( * ) Notice: Subject to any disclaimer, the term of this patent is extended or adjusted under 35 U.S.C. 154(b) by 676 days.

(21) Appl. No.: 16/668,858

(22) Filed: Oct. 30, 2019

(65) Prior Publication Data
US 2020/0132681 A1    Apr. 30, 2020

Related U.S. Application Data

(60) Provisional application No. 62/752,664, filed on Oct. 30, 2018.

(51) Int. Cl.
*G01N 33/543*   (2006.01)
*G01N 27/02*    (2006.01)
(Continued)

(52) U.S. Cl.
CPC ..... *G01N 33/54313* (2013.01); *G01N 27/026* (2013.01); *G01N 27/3276* (2013.01); *G01N 27/48* (2013.01)

(58) Field of Classification Search
CPC ......... G01N 33/54313; G01N 27/3276; G01N 33/5438
See application file for complete search history.

(56) References Cited

U.S. PATENT DOCUMENTS

2007/0265197 A1*  11/2007  Furgeson ........... A61K 47/6435
                                                              514/1.2
2011/0210017 A1*  9/2011  Lai ....................... C07D 249/04
                                                              205/792
(Continued)

OTHER PUBLICATIONS

Hyun (J. Hyun, Capture and Release of Protein on the Nanoscale by Stimuli-Responsive Elastin-Like Polypeptide "Switches", 2004(126), p. 7330-35. (Year: 2004).*

(Continued)

*Primary Examiner* — C. Sun
(74) *Attorney, Agent, or Firm* — Hamilton, Brook, Smith & Reynolds, P.C.

(57) ABSTRACT

2-dimensional surfaces modified with elastin-like polymer (ELP) that transitions between states in the presence of one or more analytes are described. This transition can be monitored to identify the presence and concentration of the one or more analytes. 2-dimensional surfaces of the present disclosure may also or alternatively be configured such that when an analyte binds to ELP on the 2-dimensional surface, such binding changes a degree at which the ELP responds to various non-analyte stimuli (e.g., pH, temperature, etc.). In such examples, the 2-dimensional surface may detect the presence of analyte based on the how the ELP responds to the non-analyte stimuli. For example, ELP on a 2-dimensional surface may transition between states at a first temperature when analyte is not present (e.g., bound to the ELP). The temperature at which the ELP transitions may change based on how much analyte (e.g., what concentration of analyte) is present.

24 Claims, 26 Drawing Sheets

Specification includes a Sequence Listing.

(51) Int. Cl.
  G01N 27/327    (2006.01)
  G01N 27/48     (2006.01)

(56) References Cited

U.S. PATENT DOCUMENTS

| | | | | |
|---|---|---|---|---|
| 2012/0070912 A1* | 3/2012 | Kitsugi | ............... | G01N 33/542 436/501 |
| 2016/0168228 A1* | 6/2016 | Despanie | ............ | C07K 14/805 435/69.7 |

OTHER PUBLICATIONS

N. Nath, Fabrication of a Reversible Protein Array Directly from Cell Lysate Using a Stimuli-Responsive Polypeptide, Anal. Chem. 2003(75), p. 709-15. (Year: 2003).*

J. Hyun, Capture and Release of Protein on the Nanoscale by Stimuli-Responsive Elastin-Like Polypeptide "Switches", 2004(126), p. 7330-35. (Year: 2004).*

K. Trabbic-Carlson, Effect of protein fusion on the transition temperature of an environmentally responsive elastin-like polypeptide: a role for surface hydrophobicity? Protein Engineering, Design & Selection 2004(17), p. 57-66. (Year: 2004).*

Bennink, M.L. et al., "Analysis of Protein-DNA Interactions by Optical Tweezers: Application to Chromatin Fibers." (2005) pp. 415-427.

Halpern, J.M. et al., "Controlling the Sensing Properties of Silicon Nanowires via the Bonds Nearest to the Silicon Nanowire Surface." ACS Appl. Mater. Interfaces 7, 11315-11321 (2015).

Halpern, J.M. et al., "Kinetic and Adsorption Studies of Biogenic Amine Neurotransmitters at Polycrystalline Diamond Microelectrodes. ECS Trans." 3, 47-57 (2007).

Hassouneh, W. et al., "Elastin-Like Polypeptides as a Purification Tag for Recombinant Proteins." Current Protocols in Protein Science 6.11.1-6.11.16, Aug. 2010.

Marvin, et al., "Flow imaging microscopy as a novel tool for high-throughput evaluation of elastin-like polymer coacervates." PLOS One (2019), 21 pages.

Tsujishita, Y. et al., "Structure and lipid transport mechanism of a StAR-related domain." Nat. Struct. Biol. 7, 408-414 (2000).

Wang, J. et al., "Ultrasensitive Electrical Biosensing of Proteins and DNA: Carbon-Nanotube Derived Amplification of the Recognition and Transduction Events." J. Am. Chem. Soc. 126, 3010-3011 (2004).

Koh, W.P. et al., "Plasma carotenoids and risk of acute myocardial infarction in the Singapore Chinese Health Study." Nutr. Metab. Cardiovasc. Dis. 21, 685-690 (2011).

Kowalczyk T.; Hnatuszko-Konka, K.; Gerszberg, A.; Kononowicz, A. K. Elastin-like Polypeptides as a Promising Family of Genetically-Engineered Protein Based Polymers. World J. Microbiol. Biotechnol. 2014, 30 (8), 2141-2152. https://doi.org/10.1007/s11274-014-1649-5.

Li, B., Vachali, P. et al., "Identification of StARD3 as a Lutein-binding Protein in the macula of the Primate Retina." Biochemistry 50, 2541-2549 (2013).

Luan, C., et al., "Solvent Deuteration Enhancement of Hydrophobicity: DSC Study of the Inverse Temperature Transition of Elastin-Based Polypeptides." J. Phys. Chem. 1991, 95 (20), 7896-7900.

Lyskawa, J. et al., "Direct Modification of a Gold Electrode with Aminophenyl Groups by Electrochemical Reduction of in Situ Generated Aminophenyl Monodiazonium Cations." Chem. Mater. 18, 4755-4763 (2006).

Macewan, S. R., et al. "Elastin-like Polypeptides: Biomedical Applications of Tunable Biopolymers." Biopolymers 2010, 94 (1), 60-77. https://doi.org/10.1002/bip.21327.

Mack, Alexis et al. "Troubleshooting the Process of Creating an Electrochemically Active Elastin-Like Polymer" Biochemistry and Molecular Biology, Apr. 20, 2018, ASBMB Presentation Abstract only.

Mares-Perlman, J. et al., "The body of evidence to support a protective role for lutein and zeaxanthin in delaying chronic disease." Overview. J. Nutr. 132, 518S-524S (2002).

Marvin, L. et al., "Flow Imaging Microscopy as a Novel Tool for High-Throughput Evaluation of Elastin-like Polymer Coacervates." PLoS One 14(5), published May 9, 2019, e0216406. https://doi.org/10.1371/journal.pone.0216406, ChemRxiv 2018. Doi.org/10.26434/chemrxiv.7367708.vl.

Mayne, S. T. et al., "Beta-carotene, carotenoids, and disease prevention in humans." FASEB J. 10, 690-701 (1996).

Mayne, S.T., et al., "Resonance Raman spectroscopic evalution of skin carotenoids as a biomarker of carotenoid status for human studies." Arch. Biochem. Biophys. 539, 163-170 (2013).

McDaniel, J. R.; Callahan, D. J.; Chilkoti, A. Drug Delivery to Solid Tumors by Elastin-like Polypeptides. Adv. Drug Deliv. Rev. 2010, 62 (15), 1456-1467. https://doi.org/10.1016/j.addr.2010.05.004.

Morales, et al., Stimulus Response Characterization of Surface-Immobilized Elastin-Like-Polymers using Electrochemical Impedance Spectroscopy, UNH Poster Presentation, Dec. 2017.

Morales, M. Stimulus Response Characterization of Surface-Immobilized Elastin-Like-Polypeptides, Presentation Dec. 2018.

Morales, M. et al., "Electrochemical characterization of the stimuli-response of surface-immobilized elastin-like polymers." Soft Matter, Royal Society of Chemistry, 2019, 9640-9646.

Morales, M. A.; Halpern, J. M. Guide to Selecting a Biorecognition Element for Biosensors. Bioconjug. Chem. 2018, 29 (10), 3231-3239. https://doi.org/10.1021/acs.bioconjchem.8b00592.

Munter, L. De, et al., "Vitamin and carotenoid intake and risk of head-neck cancer subtypes in the Netherlands Cohort Study." Am. J. Clin. Nutr. (2015). doi:10.3945/ajen.114.106096.

Nakanishi, K., et al., "On the Adsorption of Proteins on Solid Surfaces, a Common but Very Complicated Phenomenon." J. Biosci. Bioeng. 91, 233-244 (2001).

Nettles, D. L.; Chilkoti, A.; Setton, L. A. Applications of Elastin-like Polypeptides in Tissue Engineering. Adv. Drug Deliv. Rev. 2010, 62 (15), 1479-1485. https://doi.org/10.1016/j.addr.2010.04.002.

Neuman, K.C. et al., "Single-molecule force spectroscopy: optical tweezers, magnetic tweezers and atomic force microscopy." Nat. Methods 5, 491-505(2008).

Nisar, N. et al., "Carotenoid Metabolism in Plants." Mol. Plant 8, 68-82 (2015).

Nolan, J. M. et al., "Macular Pigment, Visual Function, and Macular Disease among Subjects with Alzheimer's Disease: An Exploratory Study." J. Alzheimer's Dis. 42, 1191-1202 (2014).

Norman, L. L. et al., "Redox Actuation of a Microcantilever Driven by a Self-Assembled Ferrocenylundecanethiolate Monolayer: An Investigation of the Origin of the Micromechanical Motion and Surface Stress." J. Am. Chem. Soc. 131, 2328-2337 (2009).

Ostuni, E. et al., "Adsorption of proteins to hydrophobic sites on mixed self-assembled monolayers." Langmuir 19, 1861-1872 (2003).

Palla, K. S. et al., "Optimization and Expansion of a Site-Selective N-Methylpyridinium-4-carboxaldehyde-Mediated Transamination for Bacterially Expressed Proteins." J. Am. Chem. Soc. 137, 1123-1129 (2015).

Penu, R. et al. "Application of an optimized electrochemical sensor for monitoring astaxanthin antioxidant properties against lipoperoxidation." New J. Chem. 39, 6428-6436 (2015).

Petitdemange, R.; Garanger, E.; Bataille, L.; Dieryck, W.; Bathany, K.; Garbay, B.; Deming, T. J.; Lecommandoux, S. Selective Tuning of Elastin-like Polypeptide Properties via Methionine Oxidation. Biomacromolecules 2017, 18 (2), 544-550.https://doi.org/10.1021/acs.biomac.6b01696.

Qureshi, A. et al., "Biosensors for cardiac biomarkers detection: A review." Sensors Actuators B Chem. 171-172, 62-76 (2012).

Rao, A. et al., "Carotenoids and human health". Pharmacol Research 55, 207-216 (2007).

Rissanen, T. H. et al., "Low serum lycopene concentration is associated with an excess incidence of acute coronary events and stroke: the Kuopio Ischaemic Heart Disease Risk Factor Study." Br. J. Nutr. 85, 749-754 (2001).

Roberts, S.; Dzuricky, M.; Chilkoti, A. Elastin-like Polypeptides as Models of Intrinsically Disordered Proteins. FEBS Lett. 2015, 589, 2477-2486.

(56) References Cited

OTHER PUBLICATIONS

Rodriguez-Amaya, D. B. "Quantitative analysis, in vitro assessment of bioavailability and antioxidant activity of food carotenoids—A review." J. Food Compos. Anal. 23, 726-740 (2010).

Rodriguez-Cabello, J. C. et al., "Elastin-like Polypeptides in Drug Delivery." Adv. Drug Deliv. Rev. 2016, 97, 85-100. https://doi.org/.1037//0033-2909.126.1.78.

Rodriguez-Cabello, J. C. et al., "Bioactive Scaffolds Based on Elastin-like Materials for Wound Healing." Adv. Drug Deliv. Rev. 2018, 129, 118-133.

Ruff, K. M.; Roberts, S.; Chilkoti, A.; Pappu, R. V. Advances in Understanding Stimulus-Responsive Phase Behavior of Intrinsically Disordered Protein Polymers. J. Mol. Biol. 2019, 430 (23), 4619-4635.

Ruiz Rejon,F. et al., "Plasma status of retinal, alpha- and gamma-tocopherols, and main carotenoids to first myocardial infarction: case control and follow-up study." Nutrition 18, 26-31 (2002).

Scarmo, S. et al. "Single v. multiple measures of skin carotenoids by resonance Raman spectroscopy as a biomarker of usual carotenoid status. Br. J. Nutr. 110, 911-917 (2013gle v. multiple measures of skin carotenoids by resonance Raman spectroscopy as a biomarker of usual carotenoid status." Br. J. Nutr. 110, 911-917 (2013).

Shaevitz, J.W. "A Practical Guide to Optical Trapping." (2006).

Urry, D. W. Entropic Elastic Processes in Protein Mechanisms. I. Elastic Structure Due to an Inverse Temperature Transition and Elasticity Due to Internal Chain Dynamics. J. Protein Chem. 1988, 7 (1), 1-34.

Urry, D. W. et al., "Reduction-driven polypeptide folding by the delta Tt mechanism." Biochem Biophys Res Commun 188, 611-617 (1992).

Urry, D. W., et a., "Delineation of Electrostatic and Hydrophobic-Induced PKa Shifts in Polypentapeptides: The Gluatmic Acid Residue." J. Am. Chem. Soc. 1993, 115 (16), 7509-7510.

Vachali, P. P., et al., "Surface plasmon resonance (SPR)-based biosensor technology for the quantitative characterization of protein-carotenoid interactions." Arch. Biochem. Biophys. 572, 66-72 (2015).

Valiaev, A. et al., "Microcantilever Sensing and Actuation with End-Grated Stimulus-Responsive Elastin-Like Polypeptides." Langmuir 23, 339-344 (2007).

Valiaev, A., et al., "Hydration and conformational mechanics of single, end-tethered elastin-like polypeptides." J. Am. Chem. Soc. 130, 10939-10946 (2008).

Watkins, H. M. et al., "Experimental Measurement of Surface Charge Effects on the Stability of a Surface-Bound Biopolymer." Langmuir 2018, 34 (49), 14993-14999. https://doi.org/10.1021/acs.langmuir.8b01004.

Wertz, C. F. C. et al., "Adsorption and Reorientation Kinetics of Lysozyme on Hydrophobic Surfaces." Langmuir 18, 1190-1199 (2002).

Amorim-Carrilho, K. T. et al., "Review of methods for analysis of carotenoids." Trends Anal. Chem. 56, 49-73 (2014).

Balog, E. R. et al., Stimuli-Responsive Genetically Engineered Polymer Hydrogel Demonstrates Emergent Optical Responses. ACS Biomater. Sci. Eng. 2016, 2 (7), 1135-1142. https://doi.org/10.1021/acsbiomaterials.6b00137.

Bao, J. et al. "ELP-OPH/BSA/TiO2 nanofibers/c-MWCNTs based biosensor for sensitive and selective determination of p-nitrophenyl substituted organophosphate pesticides in aqueous system" Biosensors and Bioelectronics, vol. 85, Nov. 15, 2016, pp. 935-942.

Bath, B. D. et al., "Subsecond adsorption and desorption of dopamine at carbon-fiber microelectrodes." Anal. Chem. 72, 5994-6002 (2000).

Bekard, I. et al., "Electric field induced changes in protein conformation." Soft Matter 10, 431-437 (2014).

Bidwell, G. L.; Raucher, D. Cell Penetrating Elastin-like Polypeptides for Therapeutic Peptide Delivery. Adv. Drug Deliv. Rev. 2010, 62 (15), 1486-1496. https://doi.org/10.1016/j.addr.2010.05.003.

Biswal, S. "Oxidative stress and astaxanthin: The novel supernutrient carotenoid." Int. J. Heal. Allied Sci. 3, 147-153 (2014).

Cai, D. et al., "A molecular-imprint nanosensor for ultrasensitive detection of proteins." Nat. Nanotechnol. 5, 597-601 (2010).

Callahan, D. J. et al. "Triple stimulus-responsive polypeptide nanoparticles that enhance intratumoral spatial distribution." Nano Lett. 12, 2165-2170 (2012).

Cecconi, C. et al., "Direct observation of the three-state folding of a single protein molecule." Science (80-.).309,2057-2060 (2005).

Cernocka, H. et al., "Protein structural transition at negatively charged electrode surfaces. Effects of temperature and current density." Electrochim. Acta 174, 356-360 (2015).

Cho, Y. et al., "Effects of Hofmeister Anions on the Phase Transition Temperature of Elastin-like Polypeptides." J. Phys. Chem. B 112, 13765-13771 (2008).

Cianci, M. et al., "The molecular basis of the coloration mechanism in lobster shell: betacrustacyanin at 3.2-A resolution." Proc. Natl. Acad. Sci. U. S. A. 99, 9795-9800 (2002).

Clarke, J. B. et al., "Alternative ligands as probes for the carotenoid-binding site of lobster carapace crustacyanin." Biochem. J. 265, 919-921 (1990).

Colman-Martínez, M. et al., "A New Method to Simultaneously Quantify the Antioxidants: Carotenes, Xanthophylls, and Vitamin A in Human Plasma." Oxidative Medicine and Cellular Longevity 1-10 (2015).

Dash, B. C.; Mahor, S.; Carroll, O.; Mathew, A.; Wang, W.; Woodhouse, K. A.; Pandit, A. Tunable Elastin-like Polypeptide Hollow Sphere as a High Payload and Controlled Delivery Gene Depot. J. Control. Release 2011, 152, 382-392. https://doi.org/10.1016/j.jconrel.2011.03.006.

Di Mascio, P. et al., "Antioxidant defense systems: The role of carotenoids, tecopherols, and thiols." Am. J. Clin. Nutr. 53, 194S-200S (1991).

Drummond, T. G. et al., "Electrochemical DNA sensors." Nat. Biotechnol. 21, 1192-1199 (2003).

Ermakov, I. V. et al., "Validation model for Raman based skin carotenoid detection." Arch. Biochem. Biophys. 504, 40-49 (2010).

Ermakov, I.V. et al., "Resonance Raman detection of carotenoid antioxidants in living human tissue." J. Biomed. Opt. 10, 064028 (2005).

Eyer, P.; Worek, F.; Kiderlen, D.; Sinko, G.; Stuglin, A.; Simeon-Rudolf, V.; Reiner, E. Molar Absorption Coefficients for the Reduced Ellman Reagent: Reassessment. Anal. Biochem. 2003, 312 (2), 224-227. https://doi.org/10.1016/S0003-2697(02)00506-7.

Fazal, F.M. et al., "Optical tweezers study life under tension." Nat. Photonic 5, 318-321 (2011).

Ferrari, M. et al., "Structural characterization of recombinant crustacyanin subunits from the lobster Homarus americanus." Acta Crystallogr. Sect. F. Struct. Biol. Cryst. Commun. 68, 846-853 (2012).

Fiedor, J. et al., "Potential Role of Carotenoids as Antioxidants in Human Health and Disease." Nutrients 6, 466-488 (2014).

Flavel, B. S. et al., "A Simple Approach to Patterned Protein Immobilization on Silicon via Electrografting from Diazonium Salt Solutions." ACS Appl. Mater. Interfaces 2, 1184-1190 (2010).

Garner, B. W. et al., "Electric field enhanced photoluminescence of CdTe quantum dots encapsulated in poly (N-isopropylacrylamide) nano-spheres." Opt. Express 16, 19410-19418 (2008).

Ghosh, K. et al., "Multicolor Luminescence from Conjugates of Genetically Encoded Elastin-like Polymers and Terpyridine-Lanthanides." Macromol. Chem. Phys. 216, 1856-1861 (2015).

Ghosh, K. et al., "Temperature-dependent morphology of hybrid nanoflowers from elastin-like polypeptides." APL Mater. 2, 021101 (2014).

Goode, J. A. et al., "Biosensor Regeneration: A Review of Common Techniques and Outcomes." Langmuir 2015, 31 (23), 6267-6276. https://doi.org/10.1021/la503533g.

Gray, J. J. "The interaction of proteins with solid surfaces." Curr. Opin. Struct. Biol. 14, 110-115 (2004).

Gronbeck, H. et al., "Thiols and Disulfides on the Au ( 111 ) Surface: The Headgroup—Gold Interaction Interaction." J. Am. Chem. Soc. 2000, 122 (16), 3839-3842.

Guerin, M. et al., "Haematococcus astaxanthin: applications for human health and nutrition. Trends Biotechnol." 21, 210-216 (2003).

Gulcin, I. "Antioxidant activity of food constituents: an overview." Arch. Toxicol. 86, 345-391 (2012).

(56) References Cited

OTHER PUBLICATIONS

Halpern, J. M. et al., "Diamond electrodes for neurodynamic studies in Aplysia californica." Diam. Relat. Mater. 1.5, 183-187 (2006).

Halpern, J.M. et al., "Rhenium alloys as ductile substrates for diamond thin film electrodes." Diam. Relat. Mater. 42, 33-40 (2014).

Hassouneh, W. et al., "Calcium binding peptide motifs from calmodulin confer divalent ion selectivity to elastin-like polypeptides." Biomacromolecules 14, 2347-2353 (2013).

Hassouneh, W. et al., "Elastin-like Polypeptides as a Purification Tag for Recombinant Proteins." Curr. Protoc. Protein Sci. 2010, Chapter 6, Unit 6.11. https://doi.org/10.1002/0471140864.ps0611s61.

Hoeve, C. A. et al., "The Elastic Properties of Elastin." Biopolymers 13, 677-686 (1974).

Howells, O. et al., Measuring macular pigment optical density in vivo: A review of techniques. Graefe's Arch. Clin. Exp. Ophthalmol. 249, 315-347 (2011).

Huang, H.-C.; Koria, P.; Parker, S. M.; Selby, L.; Megeed, Z.; Rege, K. Optically Responsive Gold Nanorod-Polypeptide Assemblies. Langmuir 2008, 24 (24), 14139-14144. https://doi.org/10.1021/la802842k.

Hyun, J. et al., "Capture and Release of Proteins on the Nanoscale by Stimuli-Responsive Elastin-like Polypeptide Switches." J. Am. Chem. Soc. 2004, 126 (23), 7330-7335.

Jagannathan, B. et al., "Protein folding and unfolding under force." Biopolymers 99, 860-869 (2013).

Ji, H. et al., "Microcantilever biosensors based on conformational change of proteins." Analyst 133, 434-443 (2008).

Khachik, F. "Distribution and metabolism of dietary carotenoids in humans as a criterion for development of nutritional supplements." Pure Appl. Chem. 78, 1551-1557 (2006).

Khachik, F. et al. "Identification, quantification, and relative concentrations of carotenoids and their metabolites in human milk and serum." Anal. Chem. 69, 1873-1881 (1997).

Kilmartin, P. A. "Electrochemical detection of natural antioxidants: Principles and Protocols." Antioxid. Redox Singaling 3, 941-955 (2001).

Wertz, C. F. et al., "Effect of Surface Hydrophobicity on Adsorption and Relaxation Kinetics of Albumin and Fibrinogen: Single-Species and Competitive Behavior Effect." Langmuir 2001, 17, 3006-3016.

Wightman, R. M. "Microvoltammetric Electrodes." Anal. Chem. 53, 1125A-1134A (1981).

Wightman, R. M. Voltammetry With Microscopic Electrodes in New Domains.Pdf. Science. 240, 415-420 (1988).

Winther, J. R.; Thorpe, C. Quantification of Thiol and Disulfides. Biochim. Biophys. Acta2014, 1840 (2), 838-846. https://doi.org/10.1161/ATVBAHA.114.303112.ApoA-I.

Xue, Y.; Li, X.; Li, H.; Zhang, W. Quantifying Thiol-Gold Interactions towards the Efficient Strength Control. Nat. Commun. 2014, 5. https://doi.org/10.1038/ncomms5348.

Yue, Y. et al., "Electrooxidation behavior and electrochemistry determination method of the xanthophylls: Lutein in nonaqueous media." J. Electroanal. Chem. 682, 90-94 (2012).

* cited by examiner

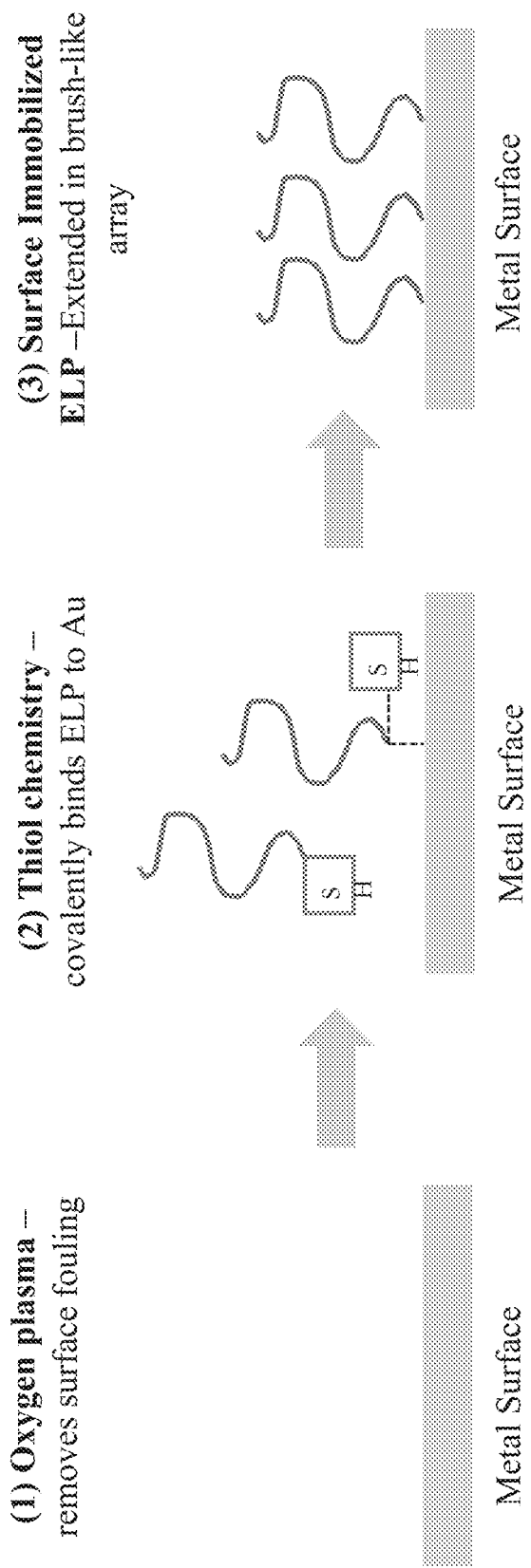

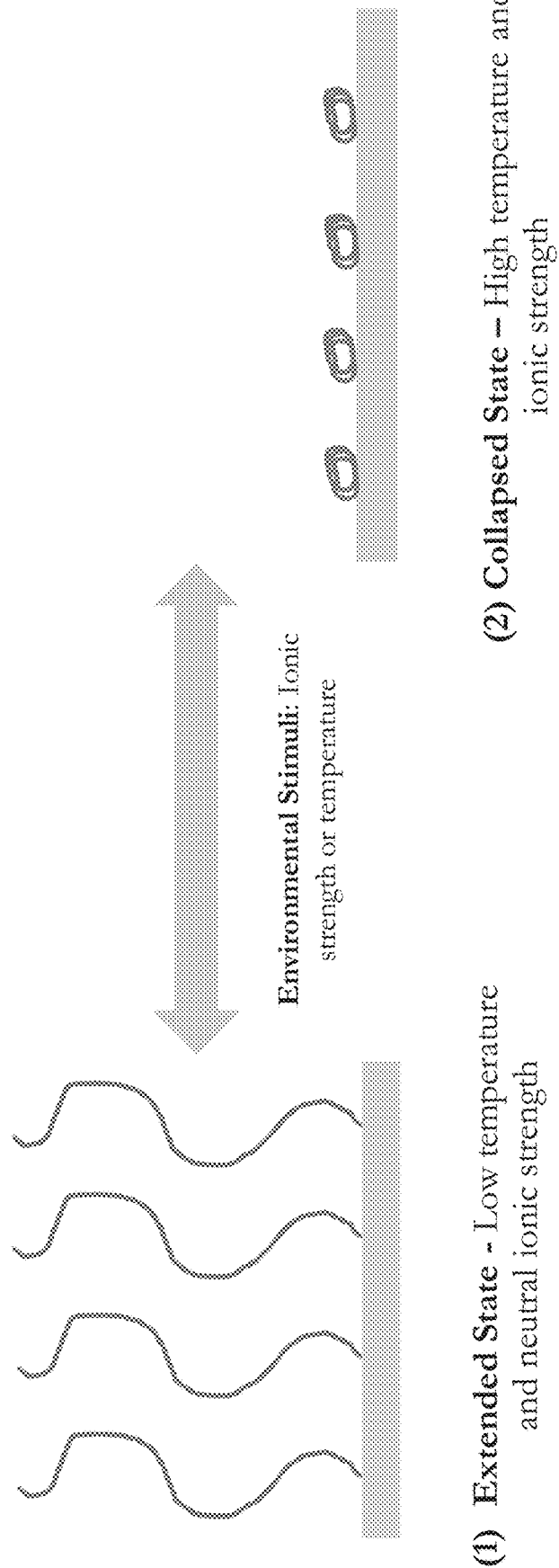

```
                        SEQUENCE LISTING

<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: X can be any amino acid except proline

<400> SEQUENCE: 1

Val Pro Gly Xaa Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 2

Val Pro Gly Val Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 3

Val Pro Gly Ile Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(5)
<223> OTHER INFORMATION: Sequence includes 40 repeats of amino acids 1-5
      in series

<400> SEQUENCE: 4

Val Pro Gly Ile Gly
1               5

<210> SEQ ID NO 5
<211> LENGTH: 5
<212> TYPE: PRT
```

```
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (1)..(5)
<223> OTHER INFORMATION: Sequence includes 90 repeats of amino acids 1-5
      in series

<400> SEQUENCE: 5

Val Pro Gly Ile Gly
1               5

<210> SEQ ID NO 6
<211> LENGTH: 200
<212> TYPE: PRT
<213> ORGANISM: Artificial Sequence
<220> FEATURE:
<223> OTHER INFORMATION: Synthetic polypeptide

<400> SEQUENCE: 6

Val Pro Gly Val Gly Val Pro Gly Val Gly Val Pro Gly Val Gly Val
1               5                   10                  15

Pro Gly Val Gly Val Pro Gly Val Gly Val Pro Gly Ala Gly Val Pro
            20                  25                  30

Gly Ala Gly Val Pro Gly Gly Val Pro Gly Gly Val Pro Gly
        35                  40                  45

Gly Gly Val Pro Gly Val Gly Val Pro Gly Val Gly Val Pro Gly Val
    50                  55                  60

Gly Val Pro Gly Val Gly Val Pro Gly Val Gly Val Pro Gly Ala Gly
65                  70                  75                  80

Val Pro Gly Ala Gly Val Pro Gly Gly Val Pro Gly Gly Gly Val
                85                  90                  95

Pro Gly Gly Gly Val Pro Gly Val Gly Val Pro Gly Val Gly Val Pro
                100                 105                 110

Gly Val Gly Val Pro Gly Val Gly Val Pro Gly Val Gly Val Pro Gly
                115                 120                 125

Ala Gly Val Pro Gly Ala Gly Val Pro Gly Gly Val Pro Gly Gly
            130                 135                 140

Gly Val Pro Gly Gly Gly Val Pro Gly Val Gly Val Pro Gly Val Gly
145                 150                 155                 160

Val Pro Gly Val Gly Val Pro Gly Val Gly Val Pro Gly Val Gly Val
                    165                 170                 175

Pro Gly Ala Gly Val Pro Gly Ala Gly Val Pro Gly Gly Gly Val Pro
            180                 185                 190

Gly Gly Gly Val Pro Gly Gly Gly
        195                 200

<210> SEQ ID NO 7
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 7

Val Pro Gly Val Gly Val Pro Gly Val Gly Val Pro Gly Val Gly Val
1               5                   10                  15

Pro Gly Val Gly Val Pro Gly Val Gly Val Pro Gly Ala Gly Val Pro
            20                  25                  30
```

-continued

Gly Ala Gly Val Pro Gly Gly Val Pro Gly Gly Val Pro Gly
        35                  40                  45

Gly Gly Val Pro Gly Val Gly Val Pro Gly Val Gly Val Pro Gly Val
    50                  55                  60

Gly Val Pro Gly Val Gly Val Pro Gly Val Gly Val Pro Gly Ala Gly
65                  70                  75                  80

Val Pro Gly Ala Gly Val Pro Gly Gly Val Pro Gly Gly Gly Val
                85                  90                  95

Pro Gly Gly Val Pro Gly Val Gly Val Pro Gly Val Gly Val Pro
            100                 105                 110

Gly Val Gly Val Pro Gly Val Gly Val Pro Gly Val Gly Val Pro Gly
        115                 120                 125

Ala Gly Val Pro Gly Ala Gly Val Pro Gly Gly Val Pro Gly Gly
    130                 135                 140

Gly Val Pro Gly Gly Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Ala Gly Val Pro Gly Ala Gly Val Pro Gly Gly Gly Val Pro
            180                 185                 190

Gly Gly Gly Val Pro Gly Gly Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Ala Gly Val Pro Gly Ala Gly Val Pro Gly Gly Gly
225                 230                 235                 240

Val Pro Gly Gly Gly Val Pro Gly Gly Gly Val Pro Gly Val Gly Val
                245                 250                 255

Pro Gly Val Gly Val Pro Gly Val Gly Val Pro Gly Val Gly Val Pro
            260                 265                 270

Gly Val Gly Val Pro Gly Ala Gly Val Pro Gly Ala Gly Val Pro Gly
        275                 280                 285

Gly Gly Val Pro Gly Gly Gly Val Pro Gly Gly Gly Val Pro Gly Val
    290                 295                 300

Gly Val Pro Gly Val Gly Val Pro Gly Val Gly Val Pro Gly Val Gly
305                 310                 315                 320

Val Pro Gly Val Gly Val Pro Gly Ala Gly Val Pro Gly Ala Gly Val
                325                 330                 335

Pro Gly Gly Gly Val Pro Gly Gly Gly Val Pro Gly Gly Gly Val Pro
            340                 345                 350

Gly Val Gly Val Pro Gly Val Gly Val Pro Gly Val Gly Val Pro Gly
        355                 360                 365

Val Gly Val Pro Gly Val Gly Val Pro Gly Ala Gly Val Pro Gly Ala
    370                 375                 380

Gly Val Pro Gly Gly Gly Val Pro Gly Gly Gly Val Pro Gly Gly Gly
385                 390                 395                 400

Val Pro Gly Val Gly Val Pro Gly Val Gly Val Pro Gly Val Gly Val
                405                 410                 415

Pro Gly Val Gly Val Pro Gly Val Gly Val Pro Gly Ala Gly Val Pro
            420                 425                 430

Gly Ala Gly Val Pro Gly Gly Val Pro Gly Gly Gly Val Pro Gly
        435                 440                 445

Gly Gly

```
450

<210> SEQ ID NO 8
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 8

Val Pro Gly Ala Gly
1               5
```

2-DIMENSIONAL SURFACES CAPABLE OF MONITORING STIMULI-RESPONSIVE BEHAVIOR AND METHODS OF USE THEREOF

RELATED APPLICATION

This application claims the benefit under 35 U.S.C. § 119(e) of U.S. Provisional application Ser. No. 62/752,664 filed Oct. 30, 2018, the disclosure of which is incorporated by reference herein in its entirety.

GOVERNMENT SUPPORT

This invention was made with government support under 1638896 awarded by the National Science Foundation. The government has certain rights in the invention.

BACKGROUND OF THE INVENTION

Carotenoids play essential roles in physiological pathways and health. Many human cells depend on molecular oxygen, which leads to the formation of reactive oxygen species (ROS). Large amounts of ROS lead to oxidative stress and contribute to many pathogenic pathways and diseases. Carotenoids remove oxidative stress by scavenging singlet molecular oxygen and peroxyl radicals. Lower carotenoid serum levels have been found present in many patients with diseases including Alzheimer's Disease, Parkinson's Disease, cardiovascular diseases, and various types of cancers.

An example carotenoid is astaxanthin, which is present in human serum at about 2 nM to about 200 nM concentrations. Astaxanthin is readily available in human diets and is linked to diseases. Although carotenoids are linked to vitality and disease, specific information on identity, quantity, and availability of carotenoids in serum remains unknown, at least in part, due to the unavailability of a cheap, selective, quick, and effective detection method. Current techniques to monitor carotenoids include separation methods (e.g., HPLC), identification methods (e.g., orsMS), and combination methods (e.g., LC-MS). These techniques are costly, low-throughput, require skilled technicians, and do not provide truly accurate concentrations of carotenoids in natural samples. Optical techniques have also been used. However, optical characterization of carotenoids is not easily standardized. Raman spectroscopy has also been used. However, Raman spectroscopy can disrupt the concentration of carotenoids by degrading the sample.

SUMMARY OF THE INVENTION

The present disclosure provides embodiments of various 2-dimensional surfaces capable of monitoring stimuli-responsive behavior. 2-dimensional surfaces of the present disclosure provide high-throughput, sensitive, accurate, and reproducible approaches to measuring stimuli-responsive behaviors in response to various stimuli, including but not limited bioanalytes such as carotenoids, pH, temperature, and various isothermal stimuli. 2-dimensional surfaces of the present disclosure are reusable, cheaper, and faster than current sensing techniques.

According to an aspect of the invention, a 2-dimensional metal surface is provided, the surface including an elastin-like polymer (ELP) covalently attached to the 2-dimensional metal surface, the ELP configured to transition between at least two transition states in response to contact with at least one stimulus. In certain embodiments, the at least one stimulus includes at least one bioanalyte. In certain embodiments, the at least one bioanalyte includes at least one carotenoid. In some embodiments, the at least one carotenoid includes at least one astaxanthin. In some embodiments, the ELP is configured as part of a monolayer of a plurality of ELPs attached to the 2-dimensional metal surface. In some embodiments, the ELP is configured with at least one biorecognition element, wherein the biorecognition element selective binds the bioanalyte. In certain embodiments, the biorecognition element includes at least one of: an antibody, streptavidin, a crustacyanin, a carotenoid-binding protein, and one partner molecule of a two partner molecule binding pair. In some embodiments, the ELP is configured with one or more electrochemical tags. In some embodiments, the electrochemical tag is: ferrocene, a ferrocene derivative, safranin, Leishman's eosine methylene blue, or rhodamine B isothiocynate. In certain embodiments, the at least two transitional states include an elongated state and a collapsed state of the ELP. In some embodiments, the ELP is conjugated to a protein. In certain embodiments, the ELP is expressed as part of a fusion protein. In some embodiments, the protein comprises a crustacyanin. In some embodiments, the at least one stimulus includes a pH. In some embodiments, the at least one stimulus includes a temperature. In certain embodiments, the at least one stimulus includes at least one of ionic strength, ligand binding, binding to a binding partner, a light, or a magnetic force. In some embodiments, the 2-dimensional metal surface is part of an electrochemical sensor. In certain embodiments, the electrochemical sensor includes an electrode. In some embodiments, the 2-dimensional metal surface includes at least one of gold, platinum, silicon, silicon dioxide, or silver. In some embodiments, the ELP is configured to bind at least one bioanalyte. In certain embodiments, the configuration includes at least one biorecognition element attached to the ELP.

According to another aspect of the invention, a device is provided and the device includes any embodiment of the aforementioned 2-dimensional metal surface of the invention.

According to another aspect of the invention, an electrode is provided and the electrode includes any embodiment of the aforementioned 2-dimensional metal surface of the invention.

According to another aspect of the invention, a method of using a 2-dimensional metal surface capable of performing a stimulus-response interaction, is provided, the method including contacting a sample with a 2-dimensional metal surface that includes a plurality of elastin-like polymer (ELP) covalently attached to the 2-dimensional metal surface, the ELP configured to transition between at least two transition states in response to contact by at least one stimulus; and monitoring the transition state of the sample-contacted ELP using at least one electrochemical detection technique capable of detecting the transition state. In some embodiments, the monitored transition state of the contacted ELP is compared to a control transition state of the ELP not contacted with the bioanalyte, and a difference detected in the transition state of the sample-contacted ELP and the control ELP indicates the presence of the bioanalyte in the sample. In some embodiments, the at least one electrochemical detection technique includes an electrochemical impedance spectroscopy method. In certain embodiments, the at least one electrochemical detection technique includes a voltametric detection method. In some embodiments, the at least one electrochemical detection technique includes an amperometric detection method. In some embodiments, the at least one electrochemical detection technique includes a quartz crystal microbalance detection method. In certain embodiments, the sample is believed to be at risk of including the bioanalyte.

According to another aspect of the invention, a 2-dimensional metal surface is provided, the surface including an elastin-like polymer (ELP) covalently attached to a 2-dimensional metal surface, the ELP configured to bind at least one bioanalyte, wherein contacting the ELP with the at least one bioanalyte alters a transition state of the ELP. In some embodiments, the at least one bioanalyte includes at least one carotenoid. In some embodiments, the at least one carotenoid includes at least one astaxanthin. In certain embodiments, the ELP is configured as part of a monolayer of a plurality of ELPs. In some embodiments, the wherein the ELP configuration includes at least one biorecognition element attached to the ELP. In certain embodiments, the at least one biorecognition element includes: an antibody, streptavidin, a crustacyanin, a carotenoid-binding protein, and one partner molecule of a two partner molecule binding pair. In some embodiments, the ELP includes one or more electrochemical tags. In some embodiments, the electrochemical tag is: ferrocene, a ferrocene derivative, safranin, Leishman's eosine methylene blue, or rhodamine B isothiocynate. In some embodiments, the transition states include an elongated state and a collapsed state. In certain embodiments, the ELP is conjugated to a protein. In some embodiments, the ELP is expressed as part of a fusion protein. In some embodiments, the protein includes a crustacyanin polypeptide. In some embodiments, the at least one stimulus includes a pH. In certain embodiments, the at least one stimulus includes a temperature. In some embodiments, the at least one stimulus includes at least one of ionic strength, contact with a binding partner, contact with a light, and contact with a magnetic force. In some embodiments, the 2-dimensional metal surface is part of an electrochemical sensor. In certain embodiments, the electrochemical sensor includes an electrode. In some embodiments, the 2-dimensional metal surface includes at least one of gold, platinum, silicon, silicon dioxide, or silver.

According to another aspect of the invention a device is provided, the device including any embodiment of the aforementioned 2-dimensional metal surface of the invention.

According to another aspect of the invention, an electrode is provided and the electrode includes any embodiment of the aforementioned 2-dimensional metal surface of the invention.

According to another aspect of the invention, a method of using a 2-dimensional metal surface capable of performing a stimulus-response interaction is provided, the method including: contacting a sample with an elastin-like polymer (ELP) covalently attached to a 2-dimensional metal surface, the ELP configured to bind a bioanalyte, forming an ELP-bioanalyte complex; applying at least one stimulus to the 2-dimensional metal surface; and monitoring a transition state of the ELP-bioanalyte complex using at least one electrochemical detection technique capable of detecting the transition state. In some embodiments, the monitored transition state of the contacted ELP is compared to a control transition state of the ELP not contacted with the bioanalyte, and a difference detected in the transition state of the sample-contacted ELP and the control ELP indicates the presence of the bioanalyte in the sample. In certain embodiments, the at least one electrochemical detection technique includes an electrochemical impedance spectroscopy method. In some embodiments, the at least one electrochemical detection technique includes a voltammetric method. In certain embodiments, the at least one electrochemical detection technique includes an amperometric method. In some embodiments, the at least one electrochemical detection technique includes a quartz crystal microbalance method. In some embodiments, the sample is believed to be at risk of comprising the bioanalyte.

BRIEF DESCRIPTION OF SEQUENCES

SEQ ID NO: 1 is amino acid sequence in which X = is any amino acid except proline:
VPGXG.

SEQ ID NO: 2 is amino acid sequence:
VPGVG.

SEQ ID NO: 3 is amino acid sequence:
VPGIG.

SEQ ID NO: 4 is amino acid sequence of I40-ELP:
$[VPGIG]_{40}$.

SEQ ID NO: 5 is amino acid sequence of I90-ELP:
$[VPGIG]_{90}$.

SEQ ID NO: 6 is amino acid sequence of V40-ELP:
$[(VPGVG)_5(VPGAG)_2(VPGGG)_3]_4$.

SEQ ID NO: 7 is amino acid sequence of V90-ELP:
$[(VPGVG)_5(VPGAG)_2(VPGGG)_3]_9$.

SEQ ID NO: 8 is amino acid sequence:
VPGAG.

BRIEF DESCRIPTION OF THE DRAWINGS

For a more complete understanding of the present disclosure, reference is now made to the following description taken in conjunction with the accompanying drawings.

FIG. 1 is a conceptual diagram illustrating how one or more elastin-like polymer (ELPs) may be covalently attached to a 2-dimensional metal surface.

FIG. 2A is a schematic diagram illustrating different states of 2-dimensional surface bound ELP.

DETAILED DESCRIPTION

Figure 2B:
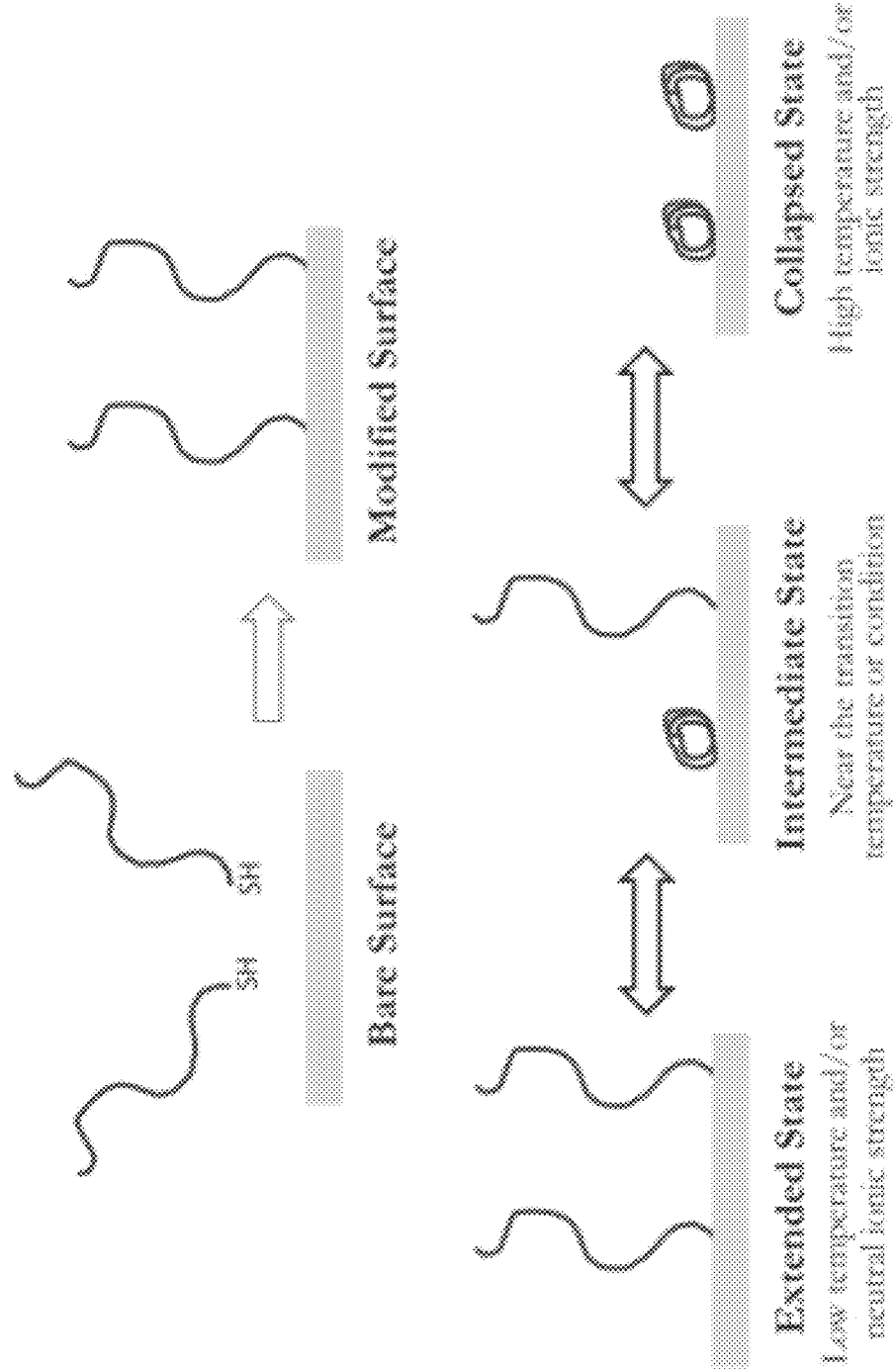
FIG. 2B provides schematic diagrams with the top row showing left to right: a bare surface is modified with a thiol to form a modified ELP surface. Bottom row shows schematic diagram showing from left to right: extended, intermediate, and collapsed conformation states.

The invention, in part relates to preparing and using 2-dimensional surfaces comprising elastin-like polymers (ELPs) that are capable of monitoring stimuli-responsive behavior. Certain aspects of the present disclosure relate to 2-dimensional surfaces capable of monitoring stimuli-responsive behavior. A 2-dimensional surface modified to include a plurality of ELPs has at least two benefits over corresponding free, ELPs in solution and use of a 2-dimensional surface modified with ELPs as described herein has advantages over detection methods comprising use of "in-solution" ELPs.

Although free-in-solution ELPs are known to have reversible coalescence behavior, sometimes such behavior is not completely reversible. The free-in-solution ELPs even if the ELP is solubilized, will coalescence to some degree. This may be especially true at higher concentrations, as higher ELP concentrations are correlative with increased coalescence and perception. In contrast, it has now been identified that that by isolating the ELP on a surface individual ELP responses are unaffected by neighboring ELPs and intermediate responses can be detected, versus the on/off detection available with free-in-solution ELPs. In addition, methods have been identified with which the ELP deposition and concentration on a 2-dimensional surface can be controlled, thus providing reproducible ELP detection on the 2-dimensional surface. Attachment to a 2-dimensional surface also permits methods of monitoring collapse of ELP on itself, which provides more specific data then prior methods of monitoring coalescence of free-in-solution ELPs.

Moreover, ELP collapse on a 2-dimensional surface could be gradual as a function of the stimulus. This is significantly different than 3-dimensional solution-based ELP coalescence. The term "3-dimensional" as used herein in reference to ELPs, means ELPs free, in-solution ELPs. The term "2-dimensional" as used herein in reference to ELPs, means ELPs attached to a surface. Solution-based ELP coalescence is typically an on-off behavior, where a stimulus will trigger the agglomeration of many ELP molecules in the solution. Because ELP on a 2-dimensional surface is unlikely to interact with neighboring ELP, the surface-attached ELPs interact with the stimulus independently. Therefore, compared to solution-based approaches, a 2-dimensional surface may create a more gradual and measurable collapse behavior that can be calibrated to the quantity of stimulus exposed to the 2-dimensional surface.

2-dimensional surfaces envisioned by the present disclosure include metal surfaces including, but not limited to surfaces comprising, gold (Au, atomic number 79), platinum (Pt, atomic number 78), silicon (Si, atomic number 14), silicon dioxide ($SiO_2$), silver (Ag, atomic number 47), and the like. 2-dimensional surfaces envisioned by the present disclosure also include non-metal surfaces, such as, but not limited to, carbon (C, atomic number 6) and the like.

In at least some embodiments, a 2-dimensional surface of the present disclosure may be configured as part of an electrochemical sensor, and more particularly, in some embodiments, as part of an electrode of an electrochemical sensor. In other words, an electrode of the present disclosure may be configured to generate different electric currents based on states of ELP bound thereto. Illustrative electrodes that may include a 2-dimensional surface of the present disclosure include, for example, gold electrodes, carbon electrodes, platinum electrodes, silicon electrodes, silicon dioxide electrodes, silver electrodes, and the like.

Previous ELP research predominantly focused on applications using free ELPs in solution with limited characterization of the stimuli-response of surface-immobilized ELPs. The present disclosure, in contrast, relates to using ELPs covalently bound to a 2-dimensional surface, for purposes of electrochemical sensing. Stimuli-response of surface-immobilized ELPs have now been characterized using electrochemical impedance spectroscopy (EIS). EIS was used to record the impedance response from an ELP modified electrode by quantifying the resistance to the flow of electrons of the redox couple at the electrode surface under an applied alternating voltage potential. An increase of impedance is expected in the collapsed state compared to the extended state as the surface-immobilized ELPs are driven to change conformation in such a way to hinder the kinetics of the redox couple exchange at the electrode interface. It has now been identified that the collapsed state of the ELPs hinders the kinetics of the redox couple exchange by decreasing the available surface area for exchange while simultaneously creating more complex diffusion pathways at the electrode surface. As set forth herein, reproducibility of an ELP surface modification has now been demonstrated and results have provided characterization of the ELP modified surface demonstrating reversibility and tunability in the stimuli-response, and previously unreported potential intermediate stimuli states.

Elastin-Like Polymers (ELPs)

A 2-dimensional surface of the present disclosure may have one or more ELPs covalently attached thereto. ELPs may be thought of as "smart polymers" that happen to be protein in origin. ELPs do not possess defined 3-D folds, domains, or hierarchical organization per se, but instead have functional resemblance to synthetic polymers such as poly(N-isopropylacrylamide) (pNIPAM) that exhibit entropy-driven stimuli-responsive behavior. Above a certain temperature (Tt, transition temperature) in aqueous environments, ELPs desolvate, condense, and aggregate. However, unlike pNIPAM, the overall ELP polarity can be manipulated, and therefore the Tt can be 'tuned,' by changing the identity of the guest residue, modifying the polypeptide, changing the salt concentration, or changing the ELP solution concentration.

ELPs lack a predefined structure, instead adopting different forms and interactions based on their environment, resulting in their stimuli-responsive properties. Above their transition temperature, ELPs will begin to aggregate, forming intermolecular contacts between their non-polar regions to prevent unfavorable interactions with their environment. The stimulus-response of ELPs can also be triggered isothermally with changes to the salt concentration or pH of the ELP environment. As non-limiting examples an ELP of the invention is contacted with a solution that has a specific salt concentration or a specific pH, and in these examples, the stimulus is the salt concentration and the pH, respectively. In some embodiments of the invention, an ELP may be contacted with a stimulus that is a bioanalye, which binds a selected biorecognition element present on the ELP.

As used herein, an "elastin-like polymer" or "ELP" refers to an intrinsically disordered polymer having pentapeptide repeats of the amino acid sequence VPGXG (SEQ ID NO: 1), where V=valine ($C_5H_{11}NO_2$), P=proline ($C_5H_9NO_2$), G=glycine ($C_2H_5NO_2$), and X=a guest position that may be occupied by any amino acid except proline.

To minimize costs of preparing 2-dimensional surfaces comprising ELPs, including but not limited to corresponding electrochemical sensors, of the present disclosure, ELPs may be produced using recombinant DNA technology in an expression system, a non-limiting example of which is an *E.coli* bacterial expression system. ELP yields in expression systems may range upwards of about 100 mg/L of expression culture. ELP may be purified to homogeneity using inverse temperature cycling, taking advantage of ELP stimuli-responsive behavior and not requiring chromatographic purification. Purity may be assessed using standard methods such as but not limited to: protein gel electrophoresis and electrospray mass spectrometry.

For example, though not intended to be limiting, an expression vector can be used to produce ELP sequences that include one or more of the pentapeptide sequences set forth as SEQ ID NO: 2 and SEQ ID NO: 3. The amino acid sequence of ELP can be programmed at the DNA level, by use of encoding sequences in expression systems and expression of the ELP sequences in such systems Those skilled in the art will know how to prepare suitable vectors and express ELP peptides that include pentapeptides such as SEQ ID NO: 2, SEQ ID NO: 3, or the general sequence VPGXG (SEQ ID NO: 1) in which "X" substituted with an amino acid other than proline, using standard expression vectors and methods. As non-limiting examples, valine or isoleucine ($C_6H_{13}NO_2$) may incorporated at the guest position, resulting in: VPGVG (SEQ ID NO: 2) and VPGIG (SEQ ID NO: 3), respectively.

ELPs are polymers comprising a plurality of pentapeptides such as those described herein. The term "subunit" is used herein in reference to one pentapeptide, for example, though not intended to be limiting, one VPGIG (SEQ ID NO: 3) pentapeptide molecule may be referred to herein as a subunit of an ELP and a plurality of subunits are included in an ELP polymer of the invention. As used herein the term "plurality" means more than one. An ELP attached to a 2-dimensional surface of the invention and/or used in a method of the invention comprises a plurality of independently selected pentapeptide subunits. It will be understood the term "independently selected" in reference to subunits means the amino acid sequence of each subunit in an ELP can be chosen and the subunits can, but need not be, all be the same. In some embodiments of an invention, an ELP includes all subunits with the same amino acid sequence. In certain embodiments of the invention an ELP may include 2, 3, 4, 5, 6, 7, or more different subunit sequences, and each may be present 1, 2, 3, 4, 5, 6, 7, or more times in the ELP. In methods of the invention and on 2-dimensional surfaces of the invention, an ELP polymer may include at least 5, 10, 15, 20, 25, 30, 35, 40, 45, 50, 55, 60, 65, 70 or more pentapeptide subunits, including all integers within this range. In some embodiments, the number of subunits in an ELP is between 35 and 50, 35 and 45, 25 and 45, 25 and 50, or is a higher number.

Non-limiting examples of ELPs that have been prepared include: I40-ELP [VPGIG]$_{40}$ (SEQ ID NO: 4); I90-ELP [VPGIG]$_{90}$ (SEQ ID NO: 5); V40-ELP [(VPGVG)$_5$(VPGAG)$_2$(VPGGG)$_3$]$_4$ (SEQ ID NO: 6); and V90-ELP

[(VPGVG)$_5$(VPGAG)$_2$(VPGGG)$_{3]9}$ (SEQ ID NO: 7). The isoleucine (I) is more hydrophobic than valine (V); and moving to larger chains will increase the hydrophobicity of the polymer allowing tunability for each application. The expected transition temperatures, (inverse to the hydrophobicity of the polymer) are I90<I40<V90<V40. Each of these polymer constructs have a cysteine (single available thiol, SH) near the N-terminus.

The net polarity of ELP can be tuned by changing the identity and mole fraction of guest residues at the $4^{th}$ position of the pentapeptide (the "X" position in SEQ ID NO: 1) while keeping polymer length constant. For example, a polymer with the composition ELP$_{40}$[V$_4$A] would have 40 subunits comprising VPGVG (SEQ ID NO: 2) and VPGAG (SEQ ID NO: 8) in a 4:1 ratio. Thus resulting in a 4:1 ratio of valine:alanine residues in the guest position over the total of 40 subunits. This polymer would be more polar than ELP$_{40}$[V$_5$], but less polar than ELP$_{40}$[V$_4$A$_2$G], which would have a 2:2:1 ratio of valine:alanine:glycine in guest positions over the same number of repeats. Polar and charged residues could also be introduced to similar effect. Those skilled in the art will recognize how to adjust polarity and charge using routine methods.

Attachment of ELPs to a 2-Dimensional Surface

One or a plurality of ELPs may be covalently attached to a 2-dimensional surface. FIG. 1 illustrates an example method for attaching one or more ELPs to a 2-dimensional metal surface. In at least some embodiments of the invention, a 2-dimensional metal surface may treated to remove surface fouling, a treatment referred to herein as polishing to remove surface fouling. Such polishing may be performed using oxygen plasma, for example, or with another suitable art-known method. After polishing the 2-dimensional metal surface, in at least some embodiments, ELPs are immobilized (also referred to herein as "attached") onto the 2-dimensional surface. In certain methods of the invention an ELP includes a functional group that permits attachment of the ELP to the 2-dimensional surface. A non-limiting example of a functional group that can be used is a thiol. In certain embodiments of the invention, a cysteine residue is included near the N-terminus of an ELP for immobilization of the ELP on a gold surface through the gold-thiol interaction. In some embodiments of the invention thiol chemistry is used to immobilize (e.g., through covalent binding) ELPs containing thiol to the 2-dimensional metal surface and a mixture of ELP-thiol is contacted with the 2-dimensional metal surface. In some attachment methods, an ELP-thiol mixture is prepared with a solution containing ELP and a reducing agent. In a non-limiting example, an ELP-thiol mixture is created using about 0.05 mg/mL ELP in about 3.5 mM of a reducing agent. One example of a reducing agent that can be used in methods of the invention is tris(2-carboxyethyl)phosphine (TCEP), which is a reducing agent that prevents formation of disulfide bonds between free ELP in solution.

The 2-dimensional metal surface may, in at least some embodiments of the invention, be contacted with (e.g., soaked in) the ELP-thiol mixture for various amounts of time (non-limiting examples of which include about 1 hour, about 2 hours, and from about 16 hours to about 24 hours). Additional contact times may be about 3, 4, 5, 6, 7, 8, 9, 10, 11, 12, 13, 14, 16 hours, including all times within this range. Contacting of the 2-dimensional metal surface with the ELP-thiol mixture may occur at various temperatures. In some embodiments, such contacting may occur at about 4° C. After contacting, the 2-dimensional metal surface may be rinsed with one or more of dimethyl sulfoxide (DMSO), methanol, ethanol, chloroform, dimethylformamide (DMF), tetrahydrofuran (THF), or other organic solvent. Following the rinse, the 2-dimensional surface is optionally sonicated. In some embodiments the 2-dimensional surface is not sonicated, which may, in some instances be based on a desire to reduce a risk of damaging attachment of the ELP(s) to the 2-dimensional metal surface with sonication. After the rinse with or without the sonication step, the result is an ELP-modified 2-dimensional metal surface. A result of the foregoing embodiment of methods of the invention may, in at least some embodiments, be a 2-dimensional metal surface functionalized with a monolayer of ELPs, with the ELPs being configured in an extended brush-like array (illustrated in the right most portion of FIG. 1).

In a non-limiting example of preparing an ELP electrode of the invention, a gold electrode is polished with 3 μM diamond slurry followed by 1 μM diamond slurry rinsing with methanol and deionized water. A final polish is done with 0.55 μM alumina slurry. The gold electrode is rinsed thoroughly (about 30 seconds) with deionized water before immersing in a pre-chilled polymer solution at a concentration of 0.0125 mg/mL in 3.5 mM TCEP (pH 7.4) for 30 minutes at 4° C. The modified gold electrode is rinsed thoroughly with deionized water and immediately transferred to a redox couple solution to measure impedance response.

Various electrochemical sensing techniques may be used to confirm attachment of ELP(s) to a 2-dimensional surface. As a non-limiting example, electrochemical impedance spectroscopy (EIS) may be used in embodiments of the invention. A non-limiting example is provided herein in Example 2, which describes a study in which EIS was used to confirm ELP attachment to a gold electrochemical sensor surface. Those skilled in the art will appreciate that in some embodiments of methods of the invention similar results may be obtained with other 2-dimensional metal and non-metal surfaces.

Surface Geometry

Aspects of the present disclosure relate to controlling surface geometry of ELP. Certain embodiments of the invention comprise use of methods to deposit nanoparticles onto surface in a controlled manner. For example, though not intended to be limiting, patterned gold nanoparticles may be deposited on a platinum surface via controlled electroplating. Equally spaced nanoparticles (about 10 nm in diameter) have been electroplated to a macrosurface. By controlling the spacing of gold particles, nucleus density of ELP polymers on a surface can be controlled. Certain embodiments of the invention include controlled deposition and controlled surface geometry of the ELP.

Removal of Physisorbed ELP from a 2-Dimensional Surface Modified with ELP

Certain aspects of the invention include removal of physisorbed ELP from a 2-dimensional surface modified with ELP. As used herein the term "physisorbed" means physical absorption. Physisorption is caused by the intermolecular force that exists between adsorbates and adsorbents. The adsorption is known as van der Waals adsorption and the force is called van der Waals force. Removal of physiosorbed ELP is the removal of ELP that is not covalently attached to the 2-dimensional surface. One method of removing physiosorbed ELP from a 2-dimensional surface of the invention comprises contacting the covalently attached ELP with an agent that removes materials, such as non-covalently attached ELPs that are physiosorbed to the ELP, which leaves the ELP that are bound to the 2-dimensional surface. A non-limiting example of removing physiosorbed ELP is provided in Example 3 herein, which describes a 2-dimensional surface that is modified with covalently attached ELP and there is some physisorbed ELP present. In the example, the 2-dimensional surface and ELP is contacted with (e.g., soaked in) dimethyl sulfoxide (DMSO). DMSO is a non-limiting example of an agent that can be used in methods of the invention to remove physiosorbed ELP. The use of DMSO in such methods is in part due to the ability of DMSO to dissolve proteins. DMSO can be used in certain embodiments of the invention to transition from a 2-dimensional surface modified with ELP and including physiosorbed ELP to a 2-dimensional surface with only covalently bound ELP. Those skilled in the art will appreciate that similar results may be achieved using other 2-dimensional metal and non-metal surfaces.

Stimuli-Responsive Behavior of ELP Bound to a 2-Dimensional Surface

ELP that is bound to a 2-dimensional surface, according to the present disclosure, may exhibit different conformational states. ELPs are a class of stimulus-responsive polypeptides that bury non-polar side chains within a hydrophobic core. ELPs can create distinct conformation states including, but not limited to, an extended state (whereby ELP extends away from the 2-dimensional surface, which may referred to as a "sensor surface", illustrated as "1" in FIG. 2A). An ELP may also be configured in what is referred to herein as a "collapsed" state (illustrated as "2" in FIG. 2A).

ELP exhibits an inverse temperature transition, whereby ELP becomes more ordered (e.g., transitions to the collapsed state) with increased temperature. Yet, above a certain temperature in aqueous environments, ELP de-solvates, condenses, and aggregates. The identity of the guest residue of the ELP sequence affects overall ELP polarity, and consequently also affects the transition temperature of the ELP. The surface ELP stimuli-responsive behavior can be triggered isothermally by various stimuli that change either the polarity of the ELP or its environment, including changes in pH, ionic strength, ELP or co-solute concentration, redox, ligand binding, binding to a binding partner, light, magnetic force, etc. For example, though not intended to be limiting: ELP in the extended state may correspond to neutral ionic strength, whereas ELP in the collapsed state may correspond to ionic strength. An ELP on a 2-dimensional surface of the invention can be identified as being in at least one of three surface states, also referred to herein as "transition states", is identified as elongated (above the Tt; a relaxed soluble state), intermediate (near the Tt; some relaxed and some condensed ELP) and collapsed (below the Tt; a condensed precipitated state) (see FIG. 2B).

Figure 3:
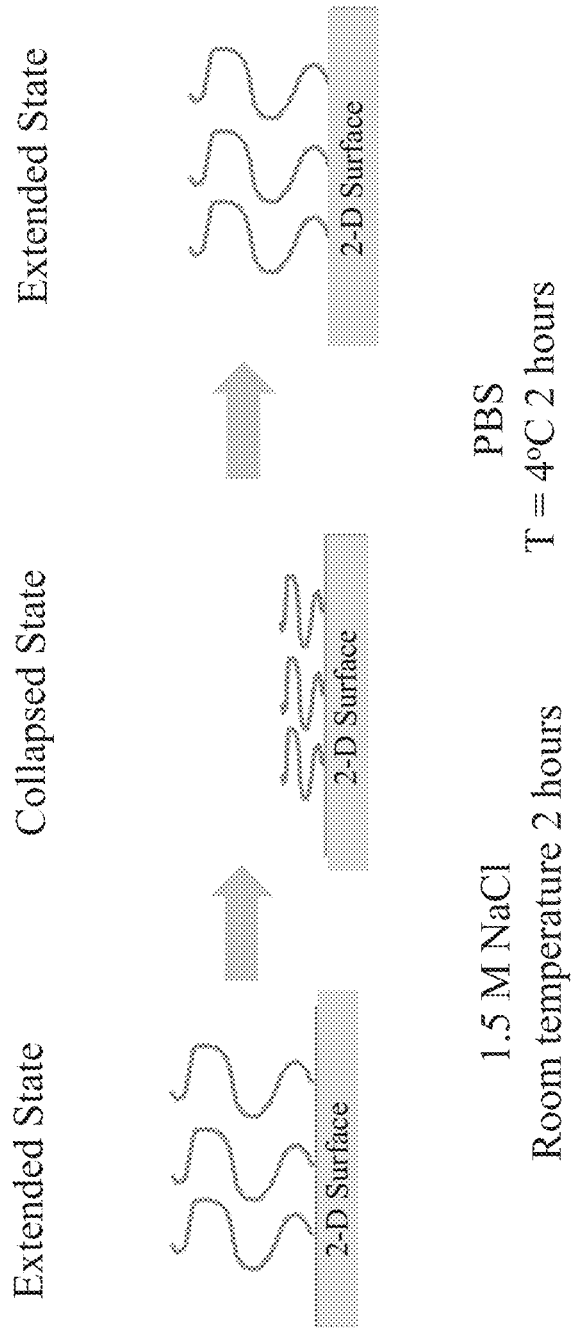
FIG. 3 is a conceptual diagram illustrating stimulus response behavior of ELP bound to a 2-dimensional surface.

FIG. 3 illustrates how ELP, bound to a 2-dimensional surface of the present disclosure, in some embodiments may respond to ionic strength and temperature. A 2-dimensional surface bound with ELP in an extended state (as illustrated by the leftmost 2-dimensional surface in FIG. 3) may be contacted with a salt solution. In at least some embodiments, such contacting may occur at about room temperature. In at least some embodiments, such contacting may occur for at least 1, 2, 3, 4, 5, 6, 7, 8, 9, 10, 20, 30, 40, 50 minutes, at least 1, 2, 3, 4, 5, 6, 7, 8, or more hours. A salt solution used in method of the invention may include one or more salts, including but not limited to sodium chloride (NaCl). The salt may be present in various concentrations, including but not limited to about 0.5M, 0.6M, 0.7M, 0.8M, 0.9M, 1.0M, 1.1M, 1.2M, 1.3M, 1.4M, 1.5 M, 1.6M, 1.7M, 1.8M, 1.9M, and 2.0M. Such contacting may cause extended ELP to transition to the collapsed state (as illustrated by the middle 2-dimensional surface in FIG. 3). The 2-dimensional surface bound with collapsed ELP may be contacted with PBS to cause the collapsed ELP to transition to the extended state (as illustrated by the rightmost 2-dimensional surface in FIG. 3). In at least some embodiments, such contacting may occur at about 4° C. In at least some embodiments, such contacting may occur for about 2 hours.

Figure 4:
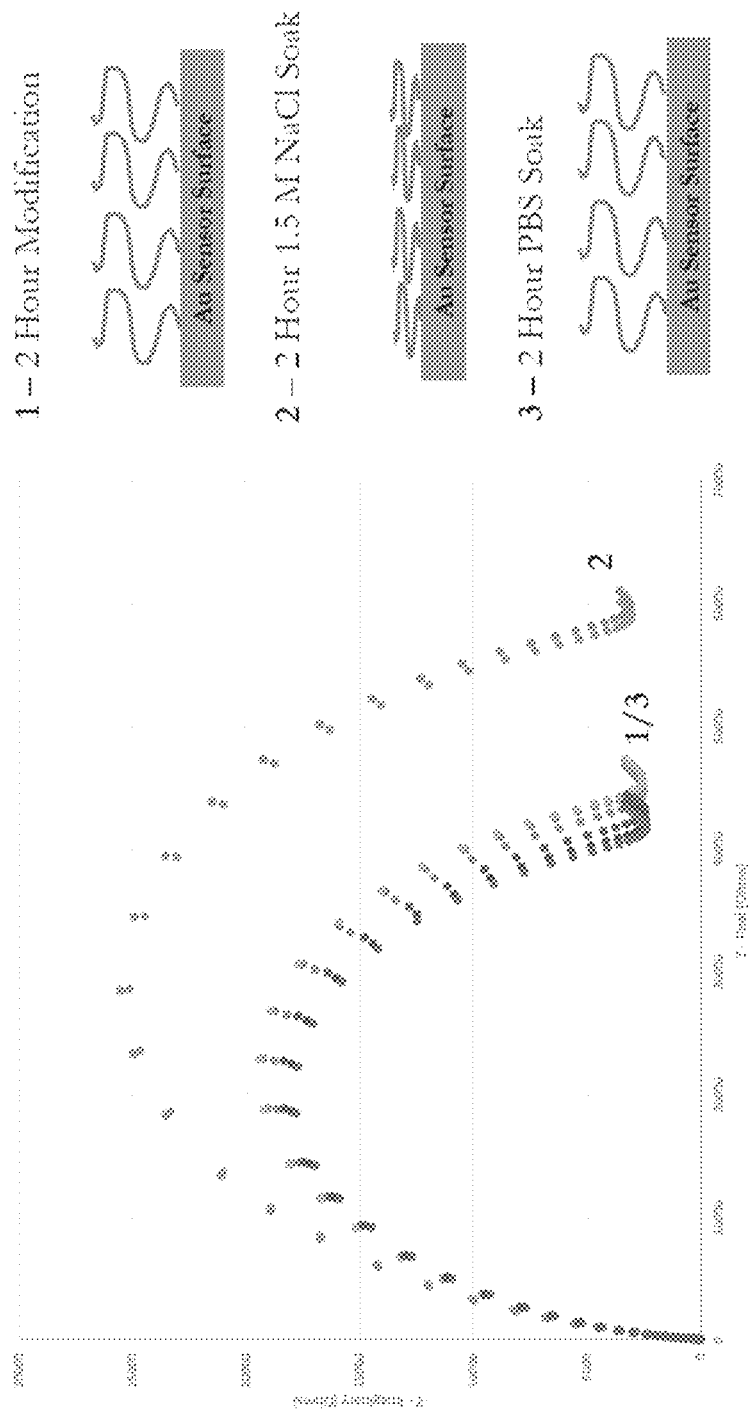
FIG. 4 is a Nyquist plot illustrating stimulus response behavior of 2-dimensional surface bound ELP in response to ionic strength.

FIG. 4 illustrates a stimulus response behavior in an embodiment of the invention comprising a gold electrochemical sensor surface bound with ELP. In this non-limiting example, a gold electrochemical sensor surface was contacted with a mixture of ELP-thiol for about 2 hours to covalently bind ELP, in the extended state, to the gold electrochemical sensor surface. "1" in FIG. 4 represents such surface and corresponding impedance measurements. "2" in FIG. 4 represents the gold electrochemical sensor surface modified with ELP in the extended state after it was contacted with about 1.5 M NaCl for about 2 hours. "3" in FIG. 4 represents the post-NaCl contacted gold electrochemical sensor surface after it was contacted with PBS for about 2 hours. The increase in impedance from 1 to 2 indicates a conformational change of ELP from the extended state to the collapsed state, with the increase in impedance likely being caused by the protein aggregate layer on the gold electrochemical sensor surface. 3 decreased back to an impedance similar to that of 1. This indicates a reversible conformational change of ELP in the presence of NaCl. Although FIG. 4 illustrates results for a gold electrochemical sensor surface, one skilled in the art will appreciate that similar results may be obtained with other 2-dimensional metal and non-metal surfaces.

In at least some embodiments, 2-dimensional surfaces of the present disclosure may be subjected to applied electric fields. It is thus envisioned that a polymer monolayer (including but not limited to ELP) applied to such 2-dimensional surface may be configured to maintain native structure and function in the presence of an applied electric field and associated local thermal changes.

Dynamic light scattering (DLS) may be used to characterize ELP stimuli-responsive behavior in the presence of electric fields. An aqueous solution of ELP may be maintained while temperature is increased step-wise in increments from about 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., and 50° C. The stimuli-responsive behavior of ELP, specifically the transition temperature, may be monitored with DLS by measuring the hydrodynamic diameter. Nanometer-scale ELP particles (e.g., monomers) may disappear over a small (e.g., about 2° C.) window to form micron-scale particles at the transition temperature, indicating collapse and aggregation of the ELP. Transition temperature may increase as ELP net polarity increases. DLS experiments for ELP constructs may be repeated under applied electric fields. Two carbon plates may be used with applied voltage from about −1 V to about +1 V. The foregoing DLS experiments provide a simple, rapid method for characterizing ELP stimuli-responsive behavior in three dimensions (e.g., ELP construct polarity, applied electric field, and temperature changes).

ELP Electrochemical Tags and Sensors

The invention, in part, includes attaching one or more agents to an ELP and method of use of such ELPs attached to 2-dimensional surfaces. In some embodiments of the invention, an ELP-modified surface is prepared and used as an electrochemical sensor. One type of agent that can be included on an ELP of the invention is referred to herein as an "electrochemical tag". Preparation steps comprise: (1) attaching an electrochemical tag to ELP to monitor the extension/collapse via cyclic voltammetry and (2) application of an electrical field or applied voltage to alter the response (stimulus state) of the electrochemically tagged ELP. Attachment of an electrochemical tag can shift the ELP's transition temperature. Further, to monitor the electrochemical tag, an applied electric field can be used. An applied electric field is also known to drive the wetting/dewetting of surface regions by reorienting the water molecules, and indirectly driving the orientation of hydrophobic polymers. ELP, in which the stimulus behavior is essentially driven between wetting/dewetting the hydrophobic regions of ELP, could be influenced by an applied electric field needed for electrochemical measurements. This permits the ELP modified surface to be manipulated and controlled with an applied electric field.

Non-limiting examples of electrochemical tags that may be used in methods and on ELPs of the invention are ferrocene ($Fe(C_5H_5)_2$) and derivatives thereof, safranin, Leishman's eosine methylene blue, and rhodamine B isothiocynate. In at least some embodiments, one or more electrochemical tags may be conjugate to the C-terminus of ELP through traditional surface modifications. In at least some embodiments, more hydrophilic electrochemical tags may result in a greater stimuli-response. These tags may be conjugated to the C-terminus of an ELP of the invention through traditional surface modifications. Specifically, Leishman's eosine, methylene blue and rhodamine B isothiocynate can be modified to the surface via standard EDC/hydrazine reaction. Safranin has a free amine that can be attached to the surface through traditional EDC/NHS chemistry. Surface conjugation can occur directly on the surface, and the modification can be confirmed by an increase in mass with eQCM-D. If needed, these polymers can be made free-in-solution and purified through size exclusion columns or dialysis.

Various strategies may be used to conjugate electrochemical tags to ELP. Protein conjugation strategies, such as amine targeting, may be used. Carboxyl-to-amine crosslinking using EDC/sulfo-NHS may be used to modify ELP with ferrocene-carboxylic acid. Multiple electrochemical tags may be placed on ELP to increase regional activity (e.g., multiple electrochemical tags may be placed on a single ELP). A significant excess of electrochemical tag may be used to avoid ELP-ELP crosslinking via protein carboxyl groups. Excess unconjugated electrochemical tag (e.g., ferrocene) may be removed after reaction using, for example, desalting columns. Conjugation efficiency may be assessed using, in at least some embodiments, mass spectrometry and absorbance at, for example, about 438 nm.

Electrochemically tagged ELP may produce a faradaic signal by transitioning between states (e.g., by collapsing or extending depending on which state the ELP is in when conjugated). In at least some embodiments, an electrochemical tag may increase the faradaic signal that would otherwise be produced from transitioning ELP without the electrochemical tag. In at least some embodiments, electrochemical quartz crystal microbalance (eQCM) may be used in conjunction with a flow cell injection apparatus to investigate the faradaic sensitivity of a 2-dimensional surface modified with such tagged (also referred to as "conjugated") ELP.

Cyclic voltammetry and amperometry are common electrochemical techniques that can be used to measure faradic response of electrochemically active materials. Cyclic voltammetry applies a triangle voltage waveform and measures the current response. Amperometry measures a current at a constant voltage; about 100 mV above the activation potential of the tag chosen will be used. A clear electrochemical faradaic current response should be observed for each electrochemical tag; increase in the current at the time of stimulus behavior should indicate an ELP collapse response.

ELP Biorecognition Elements

The invention, in part, includes attaching one or more agents to an ELP and method of use of such ELPs attached to 2-dimensional surfaces. In some embodiments of the invention, an ELP-modified surface is prepared that comprises a biorecognition element. A biorecognition element can be preselected such that it specifically binds a target agent, the biorecognition element can be included on an ELP, the ELP exposed to a sample, and if the target agent is present in the sample, it will bind the biorecognition element on the ELP, alter the configuration of the ELP, and thereby be detectable. The term "target agent" may be used interchangeably herein with the terms "analyte" and "target analyte". In certain embodiments of the invention, a biorecognition element comprises a polypeptide, which in some embodiments is produced as a fusion protein. In some embodiments of the invention, one or more biorecognition elements expressed in a fusion protein may be conjugated to a single ELP. The term "element" used in reference to a biorecognition element may comprise one of more of: a molecule, a polypeptide, a nucleic acid, a chemical, one part of a two-part binding pair, or other suitable element for use as described herein. As used herein the terms "detect" and "detecting" mean determining, for example if an analyte is detected in a sample is means it is determined as present in the sample. It will be understood that the detection and determination methods may include monitoring for a signal, a change in a signal, etc. For example, though not intended to be limiting, a transition status of an ELP comprising a biorecognition element and covalently attached to a 2-dimensional metal surface of the invention can be monitored to detect a change in a transition status of the ELP when contacted with a sample. A determined change in the transition status upon contact of the ELP with the sample, identifies the presence in the sample of an analyte that binds the biorecognition element.

A 2-dimensional surface comprising ELPs with one or more biorecognition elements can be used to assess the presence or absence of the target agent(s) in a biological sample. For example, ELPs on a 2-dimensional surface of the invention may be contacted with a sample and used to detected the presence or absence of an analyte of interest in that sample. In some embodiments of the invention a biorecognition element is selected that is known to bind an analyte of interest and the biorecognition element is attached to ELPs on the 2-dimentional surface. The binding of an analyte of interest to the biorecognition element results in a conformational change in the ELP, which is detectable using methods of the invention. In this instance, the presence of the analyte of interest is detected if the confirmation change occurs when the ELP is contacted with the sample. Similarly, the absence of the analyte of interest in the sample is confirmed by the lack of the conformation change when the ELP is contacted with the sample.

A biorecognition element and its target agent can be a pair disclosed herein, or other suitable art-known binding pair. As used herein a binding pair means a pair of molecules that selectively bind each other. A binding pair may be described herein as a "two molecule binding pair" which is understood to include two partner molecules that bind to form the binding pair. Non-limiting examples include: a streptavidin: biotin pair, in which streptavidin is one of the partner molecules of the binding pair and biotin is the other partner molecule of the binding pair. In some embodiments of the invention, one of the binding partner molecules of a binding pair is included on an ELP and also is referred to herein as a biorecognition element. The other one of the binding partners may be referred to herein as a target molecule of the biorecognition element, an analyte. In a non-limiting example, streptavidin included on the ELP as a biorecognition element and biotin is its target agent. Streptavidin is a protein purified from the bacterium Streptomyces avidinii and generally, streptavidin homo-tetramers have a high binding affinity for biotin. To conjugate ELP with streptavidin, a lysine (e.g., free amine) may be added near the C-terminus of the ELP via mutagenesis. This will create two potential modification sites (i.e., one for electrochemical tags and one for streptavidin), far from the 2-dimensional surface to which the ELP are attached. The free amine may be activated with NHS-phosphine surface crosslinker and bound to streptavidin-hydrazide. Conjugation may be confirmed with eQCM-D and Attenuated total reflectance—Fourier transform infra-red spectroscopy (ATR-FTIR).

In at least some embodiments, ELP may be conjugated with biotinylated IL-1β antibodies (IL1β-Ab) to produce ELP configured to bind cytokines. Cytokines are biomarkers that impact cell signaling and have significant impact on the immune system and cell behavior. Non-limiting examples of cytokines are IL-1β and IL-6, which have both been linked to infectious, autoimmune, and malignant disorders. IL-1β and IL-6 have also been identified as potential biomarkers for pain management, depression, schizophrenia, and inflammatory diseases (e.g., arthritis). IL-1β has been linked to opioid use disorder. Conjugation of ELP with IL1β-Ab may be confirmed with eQCM-D, ATR-FTIR, and atomic force microscopy (AFM). If a surface is tuned to elicit a collapse response after IL-1β binding, the collapse response can be measured isothermally using eQCM-F and EIS with untagged ELP and using cyclic voltammetry or amperometry with tagged ELP. The term "configured with" as used herein in relation to an ELP and a biorecognition element or an ELP and an electrochemical tag means the ELP is attached to the biorecognition element or electrochemical tag, respectively.

For tagged ELP, the faradaic response is directly linked to the collapse response (and analyte binding), but untagged ELP is more convoluted as binding of IL-1β and collapse, can cause similar signals. Therefore, in at least some embodiments, a temperature ramping may be done to ensure binding occurred; a shift in the transition temperature may be observed in complexed IL-1β to ELP:streptavidin:IL1β-Ab constructs observed with EIS. Controls may be needed, specifically, ELP:streptavidin exposed to IL-1β (no recognition element), bare electrode exposed to IL-1β (no recognition element), and bare electrode "modified" with IL1β-Ab (no attachment of recognition element to gold surface); all three controls should provide no to minimal signal after exposure to IL-1β and temperature ramping.

Another non-limiting example of a biorecognition element that can be included in an embodiment of a method of the invention, is a crustacyanin, which is a carotenoid-binding protein. The one or more biorecognition element proteins may include α-crustacyanin and/or β-crustacyanin. Such conjugated ELP may be used to detect various carotenoid target agents, including but not limited to astaxanthin (a carotenoid pigment that occurs in trout, microalgae, yeast, and shrimp). To decrease cost, crustacyanin may be produced recombinantly in E. coli using known techniques. Thus, in some embodiments, an ELP may be prepared as part of a fusion protein (i.e., a protein comprising at least 2 domains that are encoded by separate genes that have been joined so that they are transcribed and translated as a single unit, producing a single polypeptide). In certain embodiments, an ELP may be conjugated or attached to a protein using art known methods.

Although carotenoids are linked to vitality and disease, specific information on identity, quantity, and availability of carotenoid in serum remains unknown, at least in part, due to lack of a cheap, selective, quick, and effective detection method. 2-dimensional surfaces of the present disclosure provide such detection method that can be used to assess the presence or absence of carotenoids in a biological sample such as blood, urine, etc.

Another biorecognition element that may be attached to an ELP on a 2-dimensional surface of the invention is one or more of a CXCL-10 ab (CXCL-10 antibody). CXCL-10 antibodies are capable of specifically binding CXCL-10 as a target agent. Methods and 2-dimensinal surfaces comprising ELPs of the invention can be used to detect the presence or absence of a cytokine in a biological sample. CXCL-10 is from the chemokine family and is associated with an inflammatory response and can be used as a biomarker for opioid use disorder and other diseases. In some embodiments of the invention, a CXCL10-Ab is attached to a ELP on a 2-dimensional surface via streptavidin:biotin interaction. Controls, similar to those described above with respect to IL-1β detection, may be run. A sensor, configured to detect CXCL-10, would be responsive to CXCL-10, and not IL-1β because of the change in the recognition element.

As set forth herein, various strategies can be used to design and prepare a 2-dimensional surface with attached ELPs that include one component of a binding pair, wherein the binding of the two components of the binding pair results in a detectable conformational change in the ELP. This permits use of a 2-dimensional surface comprising such ELPs as a sensor that is capable of detecting the bound binding pair. Other binding pairs suitable for use in methods of the invention are known in the art.

Fusion Proteins

ELP may be expressed as part of a fusion protein using standard methods of protein production, for example using a bacterial or other expression vector.

In at least some embodiments, a 2-dimensional surface may be bound with ELP conjugated with one or more crustacyanin-ELP fusion proteins (CR-ELPs). The CR-ELPs may be modified with one or more electrochemical tags. Since CR-ELP has an additional specific ligand-binding component (i.e., CR) as compared to electrochemically tagged ELP, CR-ELP may be used as a biosensor towards bioanalytes including, but not limited to, carotenoids, such as astaxanthin.

Crustacyanin (CR) may be produced in *E.coli*. CR is generally insoluble. CR may require resolubiliation and refolding in the presence of bioanalyte, including carotenoid, and particularly astaxanthin. In some embodiments, CR may be produced in a fusion protein that also includes an ELP of the present disclosure.

Figure 13:
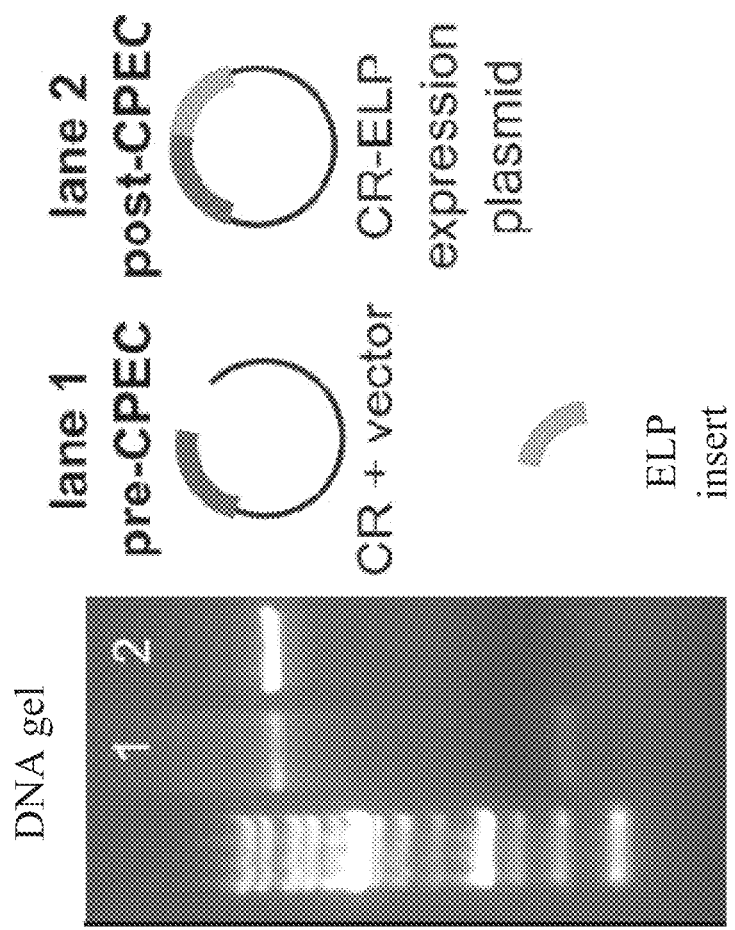
FIG. 13 illustrates a DNA gel with incorporation of the ELP gene into a $Pet_{11}b$ crustacyanin plasmid.

CR-ELP expression constructs may be made using the circular polymerase extension cloning (CPEC) method. In at least some embodiments, a gene encoding VPGIG$_{25}$ may be amplified from an ELP-containing plasmid using primers that append short sequences to each end of the ELP gene that are complementary to regions flanking the target insertion site on the CR plasmid. Inverse PCR may be used to linearize the CR plasmid. The two linear gene products, representing the ELP insert and the CR+pet$_{11}$b vector backbone, may be combined in a CPEC reaction. FIG. 13 illustrates a DNA gel with incorporation of the ELP gene into the pet$_{11}$b CR plasmid. The disappearance of the lower band indicates successful combination of the two genes, which in turn allows expression of the fusion protein.

Fusion proteins, such as CR-ELP, may possess greater diversity in amino acid composition than ELPs by themselves. This may affect the ability to place a defined number of electrochemical tags in specific locations on the protein. Using CR as a non-limiting example, CR possesses 13 solvent exposed lysine residues, which means up to 13 tags may be conjugated if NHS ester-based chemistry is used. An alternative approach is introduction of free cysteine residues to enable cysteine alkylation modification strategies. CR relies on multiple disulfide bonds for proper folding. Introduction of additional cysteine residues may disrupt native bonding patterns.

Another alternative approach is N-terminal transamination, which introduces exactly one conjugation site per fusion protein, at the N-terminus of the protein. N-terminal transamination oxidizes the N-terminal amino group, of the protein, to a reactive aldehyde or ketone. Some optimization of sequences near the N-terminus may be done to achieve higher efficiency modification. Conjugating a single tag per protein may allow for more reproducible and monodisperse stimuli-responsive behavior of the tagged protein.

A flow cell injection apparatus with eQCM may be used, in at least some embodiments, to electrochemically test detection of astaxanthin using a 2-dimensional surface having tagged fusion ELP attached thereto. The 2-dimensional surface may be tested with known stimuli (e.g., salt or temperature changes). The 2-dimensional surface may also be tested in buffered solution with various concentrations of astaxanthin. Due to solubility concerns, a relatively small amount of Tween 20 may be used. As astaxanthin binds with the electrochemically tagged fusion proteins (e.g., CR-ELPs tagged with ferrocene), the electrochemically tagged fusion proteins may transition between states (e.g., transition from the extended state to the collapsed state), thereby producing a unique electrochemical signal associated with astaxanthin concentration.

A serial dilution of astaxanthin may generate a calibration curve to determine sensitivity of the electrochemically tagged ELP to astaxanthin. These results may be used to estimate the binding rate of the electrochemically tagged ELP to astaxanthin. A logarithmic relationship may be observed. While the above describes a method of determining sensitivity of electrochemically tagged ELP to astaxanthin, one skilled in the art will appreciate that the above is merely illustrative, and that the above may be used to determine sensitivity of electrochemically tagged ELP to various analytes, including bioanalytes. The terms "analyte" and "bioanalyte" may be used interchangeably herein.

Electrochemical Sensors 2-dimensional surfaces of the present disclosure may be implemented as part of various types of electrochemical sensors. A non-limiting example of an electrochemical sensor includes an electrode. Electrodes envisioned by the present disclosure include, by way of example and not limitation, gold electrodes, carbon electrodes, platinum electrodes, silicon electrodes, silicon dioxide electrodes, silver electrodes, and the like. If implemented as a carbon electrode, thionyl chloride followed by a Grignard reaction may be used to attach ELP to a 2-dimensional carbon surface of the electrode. Alternatively, ELP may be conjugated to the carbon surface through electrografting an intermediate followed by EDC/NHS conjugation of ELP to the surface. A phenyl amine may be attached to the carbon surface using an electrografting technique via p-phenylenediamine. This intermediate may be followed by either electrochemically tagged or untagged ELP attachment.

ATR-FTIR may be used, in at least some embodiments, to confirm binding of ELP to the 2-dimensional surface. AFM may be used, in at least some embodiments, to determine roughness. X-ray phonon spectroscopy (XPS) may be used, in at least some embodiments, to determine surface coverage. XPS and conductive probe AFM may be used, in at least some embodiments, to quantify an amount of electrochemical tags (e.g., ferrocene) on ELP bound to the 2-dimensional surface. Conductive probe AFM may be used, in at least some embodiments, to characterize a spatial distribution of electrochemical tags (e.g., ferrocene) on the 2-dimensional surface at, for example, a nanometer scale.

In an eQCM setup, a resonance scan may be used to evaluate electrochemical activity of 2-dimensional surface-bound electrochemically-tagged ELP. In at least some embodiments, a resonance scan may be used to evaluate electrochemical activity of 2-dimensional surface-bound ferrocene-tagged ELP. A resonance scan may be run while cycling between PBS solution and salt (e.g., NaCl) in PBS. The salt (e.g., NaCl) may be about 1.5 M. The salt in the PBS may cause electrochemically-tagged ELP to transition from the extended state to the collapsed state. Such collapse results in a frequency shift, due to local mass changes, which may be measured by eQCM. Cyclic voltammetric techniques may, in at least some embodiments, be applied to eQCM crystals to monitor electrochemical activity. A strong faradaic response may be observed while observing an increase in resonance frequency. A loss of electrochemical response may be observed when observing a decrease in resonance frequency.

As described, ELP may transition between an extended state and a collapsed state in response to various stimuli. Either transition may be monitored depending on how the 2-dimensional surface is configured. For example, if the 2-dimensional surface is bound with ELP in the extended state, transition to the collapsed state may be observed. Conversely, if the 2-dimensional surface is bound with ELP in the collapsed state, transition to the extended state may be observed.

Various detection techniques may be used to confirm attachment of ELP to a 2-dimensional surface at each stage of the conjugation. In at least some embodiments, ATR-FTIR, AFM, and/or XPS may be used. A higher sensitivity to collapsed ELP as compared to free (e.g., not attached) ELP may be observed. As a non-limiting example, higher sensitivity to collapsed electrochemically tagged (e.g., with ferrocene) ELP as compared to unattached electrochemically tagged ELP may be observed.

An on/off faradaic correlation when ELP is triggered to collapse versus extend may be observed. The on/off measurements may be confirmed with mass changes measured using, for example, eQCM.

Specificity of 2-dimensional surfaces according to the present disclosure may be tested using various techniques. In at least some embodiments, an ELP fusion protein capable of binding to an antioxidant may be used. Such binding of antioxidant to ELP fusion protein may be monitored electrochemically.

Although the present disclosure provides embodiments of 2-dimensional surfaces and methods of their use, one skilled in the art will appreciate that other types of 2-dimensional surfaces may be configured to implement the teachings herein. If non-electrochemical sensors are used, non-electrochemical sensing techniques may be used. Numerous such techniques are known in the art and include, but are not limited to, optical techniques, fluorescent techniques, surface plasmon resonance, and others.

In at least some embodiments, an electrochemical sensor may be a multiplexed sensor. For example, arrays, in 96 well plates lined with gold, may be constructed to create a multiplex sensor for multiple analytes, via ELP response, simultaneously. In at least some embodiments, different biorecognition elements may be placed in different wells for intended analyte specificity. The analyte of interest, or unknown analyte, may be added to each well and monitored independently in a multiplex array system.

Samples

Electrochemical sensors, in accordance with the present disclosure, may be used to detect one or more analytes in one or more different samples. In at least some embodiments of the invention, a sample may be a complex media, including but not limited to biological samples. The term "biological sample" may be used herein interchangeably with the term "sample". A non-limiting list of possible biological samples includes urine, blood, plasma, saliva, exudate, phlegm, breast milk, amniotic fluid, vitriol fluid, puss, nasal discharge, biopsy material, or any other biological samples. Other biological samples may be samples that include a material obtained from a plant, soil, water, a body of water, a waterway, etc. In some embodiments a sample is an aqueous sample.

A sample that is contacted with a 2-dimensional metal surface comprising ELPs may be a naïve sample, meaning of unknown content with respect to inclusion of one or more analytes of interest. In some embodiments a sample that is contacted with a 2-dimensional metal surface comprising ELPs is a sample believed to be at risk of including one or more analytes of interest. The term "at risk of including" as used in the context of a practitioner's understanding of a sample means a one or more of: suspected of including, possibly including, and known to include an analyte of interest. In certain embodiments of the invention, a biorecognition element is selected for inclusion as part of an ELP covalently attached to a 2-dimensoinal surface of the invention based on a practitioner's understanding of a sample to be assessed using a method of the invention. As a non-limiting example, if it is expected that a sample includes a carotenoid, a carotenoid-binding protein is selected and included as a biorecognition element on an ELP attached to a 2-dimensional metal surface of the invention.

A biological sample, that may be tested using electrochemical sensors of the present disclosure, may be an aqueous sample, in at least some embodiments. A biological sample, in at least some embodiments of the invention, may be obtained from a subject.

As used herein, the term "subject" may refer to a vertebrate mammal including but not limited to a human, non-human primate (e.g., monkey), mouse, rate, guinea pig, rabbit, cow, dog, cat, horse, goat, bird, reptile, insect, or fish. A subject may be a domesticated animal, a wild animal, or an agricultural animal. Accordingly, teachings of the present disclosure may be used with respect to human and non-human subjects. For instance, teachings of the present disclosure can be used in veterinary applications (e.g., in zoos, reserves, farms, in the wild, etc.) as well as in human prevention and treatment regimens.

In at least some embodiments, a biological sample may be obtained from culture. It is within the knowledge of one skilled in the art how to obtain a biological sample from a subject or a culture. In at least some embodiments, a biological sample may be diluted prior to testing, using art known means.

EXAMPLES

Example 1

Production of I40 and I40-Blocked ELPs

The I40 polymer was synthesized as previously described (Marviin, L., et al., ChemRxiv 2018. Doi.org/10.26434/chemrxiv.7367708.v1). I40 and I40-blocked were produced, tested, and their activities compared. The I40 used in this study was an ELP that included 40 total pentapeptide repeats, an isoleucine guest residue, and a cysteine residue near the N-terminus for immobilization of the ELP on a gold surface through the gold-thiol interaction. The resulting ELP was a 210 amino acid polymer having a molecular weight of 17.8 kDa. The I40-Blocked used in this study was synthesized by alkylation of the thiol-containing cysteine residue of I40. Both the I40 and I40-blocked were produced and compared.

As detailed elsewhere herein, I40 was successfully immobilized on a gold surface and its stimuli-responsive behavior was monitored using electrochemistry. Quantifiable differences in charge transfer resistance were observed for I40-modified surfaces exposed to low versus high salt environments, suggestive of significant, dynamic changes in polymer morphology. Further electrochemical characterization of surface-immobilized I40 demonstrated a reproducible surface modification, as well as reversibility and tenability of the stimuli-responsive behavior that can be generated by promoting the intramolecular response of ELP.

Methods

Production of I40

Steps included in production of the I40 comprised the following: A POE-W I40 plasmid was transformed into BL21(DE3) *E. coli* and plated on 2xYT solid medium+carbenicillin. Starter cultures of nutrient-rich liquid medium+carbenicillin were inoculated with multiple colonies and shaken at 200 rpm at 37° C. for 2 hours to 4 hours until visible growth was detected. Cultures were transferred to 1 L volumes of the same media in 2 L flasks, which were then shaken at 200 rpm at 37° C. for 24 hours. Cells were harvested by centrifugation, and I40 were purified from the periplasmic fraction using inverse transition cycling. Purified I40 was lyophilized for long-term storage at −20° C.

Production of I40-Blocked

Steps included in production of the I40-Blocked comprised the following: Purified I40 was resuspended to a concentration of 0.2 mM in 1 mL of sterile-filtered 6 M guanidine hydrochloric acid (HCl). Dithiothreitol (DTT) was added to a concentration of 10 mM and the solution was mixed and incubated for 10 mins. Iodoacetic acid was added to a final concentration of 25 mM. The solution was mixed and placed in the dark for 30 mins. The reaction was then quenched with an additional 20 mM DTT. The resulting alkylated I40 was dialyzed into deionized water overnight at 4° C. and lyophilized.

Electrochemical Impedance Spectroscopy (EIS)

All electrochemistry was performed at the open circuit potential in a Gamry Instruments VistaShield Faraday cage with a Gamry Instruments 600+Potentiostat/Galvanostat/ZRA over a frequency range of 100,000 Hz to 0.05 Hz with an AC voltage potential of 10 mVRms. A three-electrode array was used comprised of a platinum wire counter electrode, Ag/AgCl reference electrode, and a gold working electrode (BASi, 1.6 mm rod electrode). To measure the impedance response, the modified gold electrode was removed from the test solution and transferred into a 10 mM $[Fe(CN)_6]^{3-/4-}$ redox couple solution needed to generate the flow of electrons at the electrode. Prior to recording the impedance response, high-purity nitrogen was bubbled through the 10 mM $[Fe(CN)_6]^{3-/4-}$ redox couple solution for 10 minutes to purge the system of any oxidative species. The impedance response was analyzed using Gamry EChem Analyst software.

The stimuli-response of an I40 modified electrode and an I-40-Blocked modified electrode was characterized by recording the impedance response in a 10 mM $[Fe(CN)_6]^{3-/4-}$ redox couple solution after exposing the electrode to a high salt concentration for 2 hours or to a low salt environment (0.0 M NaCl) overnight.

Atomic Force Microscopy (AFM)

Surface characterization was achieved using AFM with an Asylum Cypher ES scanning probe microscope. Imaging was performed using AC mode in deionized water using a BudgetSensors SHR150 probe driven with blueDrive photothermal excitation. A scan rate of 0.70 Hz with a 5 μm×5 μm scan size was used to produce 1024 pixel×1024 pixel images I40 ELP Construction Information The I40 polymer was designed to contain a cysteine residue at the N-terminus for immobilization of I40 on the electrode surface. Thiol chemistry was used to form a bond between the sulfur of the cysteine on I40 and the gold electrode surface. The I40-Blocked polymer, containing a modified cysteine residue, was used as a comparison to I40 to validate the thiol interaction with the gold surface.

Verification of the thiol alkylation of I40-Blocked was achieved using Ellman's Reagent 5,5'-dithiobis-(2-nitrobenzoic acid), often referred to as DTNB, to quantify the number of available thiols. The conjugate base of the free sulfhydryl groups (R-S') cleaves the disulfide bond on the DTNB to form a mixed disulfide and 2-nitro-5-thiobenzoate (TNB), a reaction product yellow in color which can be measured using spectroscopy.

Figure 14:
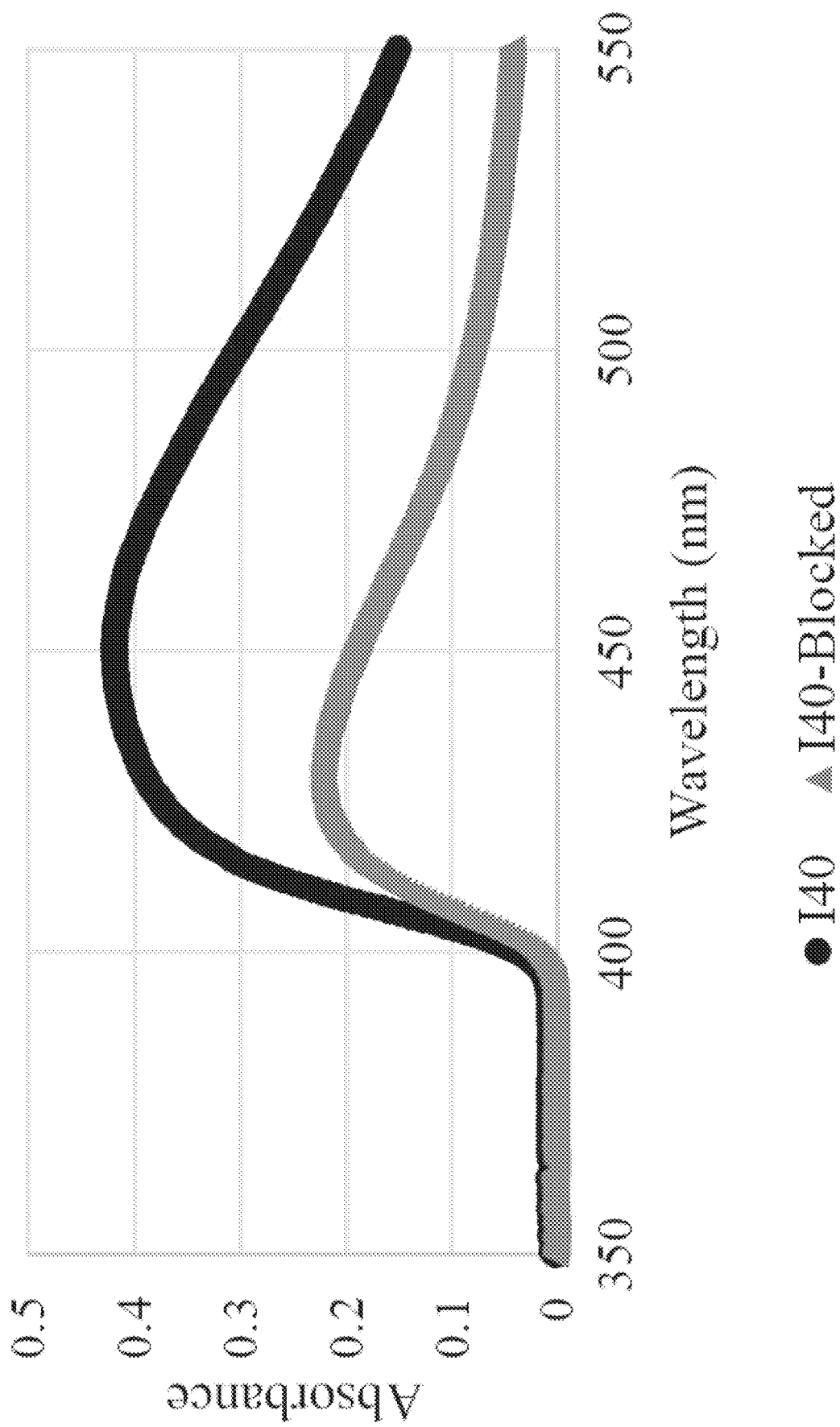
FIG. 14 is a graph illustrating a comparison of I40 and I40-Blocked ELPs after reaction with Ellman's Reagent 5,5'-dithiobis-(2-nitrobenzoic acid) (DTNB). Upper trace is I40, lower trace is I40-Blocked.

300 μL of a prechilled solution of 1.0 mg/mL I40 or I40-Blocked in 10% DMSO was mixed with 100 μL of 4 mg/mL of DTNB. The reaction proceeded on ice for 15 minutes before measuring using UV-Vis. As seen in FIG. 14, there is a decrease in absorbance for I40-Blocked polymer compared to I40, indicating a decrease in the number of available thiols on the polymer after alkylation with iodoacetamide.

Example 2

Attachment of ELP(s) to 2-Dimensional Surfaces

Means used to prepare ELPs such as, but not limited to: I40 ELPs and I40-Blocked ELPs for use these experiments are described in Example 1.

Figure 5:
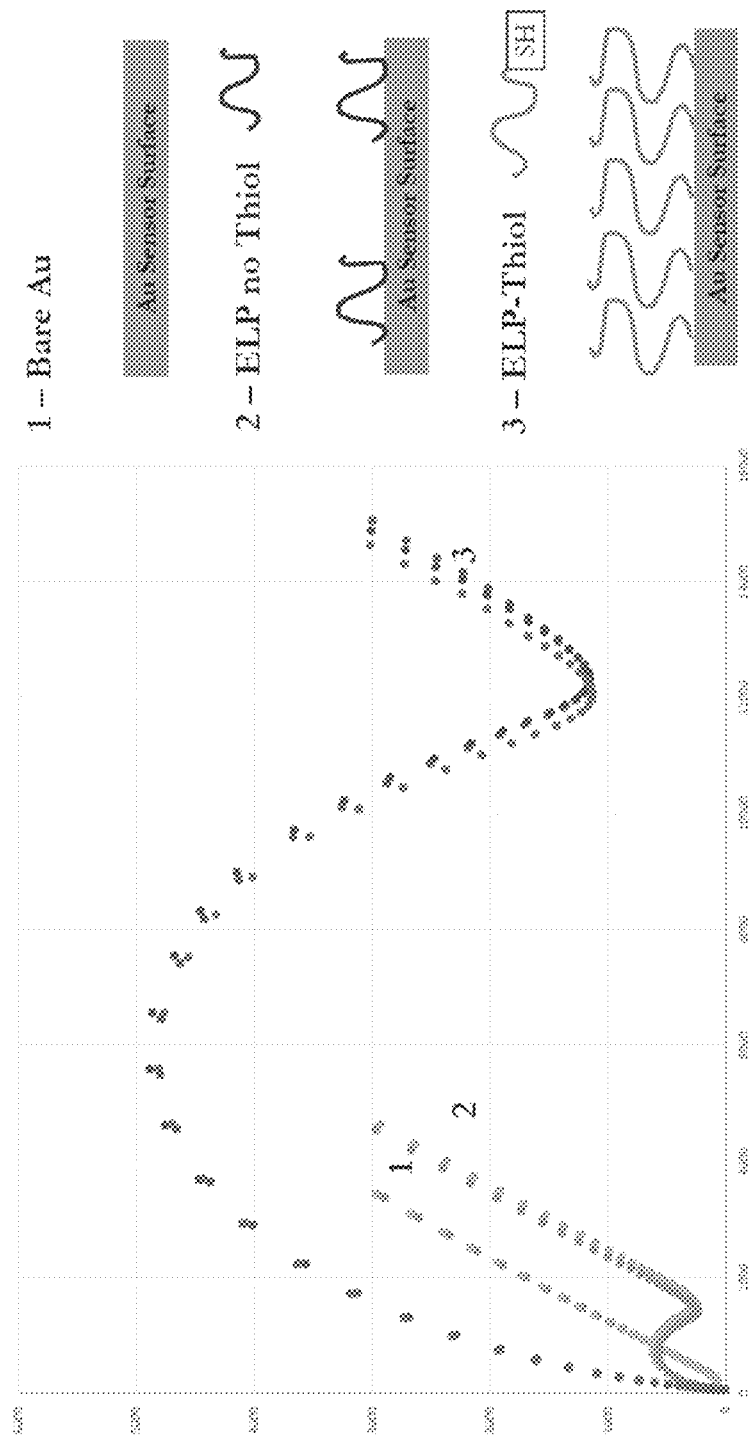
FIG. 5 is a Nyquist plot illustrating impedance of a bare gold electrochemical sensor surface, a gold electrochemical sensor surface with ELP, and a gold electrochemical sensor surface with thiol modified ELP.

Various electrochemical sensing techniques may be used to confirm attachment of ELP(s) to a 2-dimensional surface. As illustrated in FIG. 5, electrochemical impedance spectroscopy (EIS) may be used. Three different surfaces were tested in triplicate runs on a same gold electrochemical sensor surface. A bare gold electrochemical sensor surface is designated "1" in FIG. 5. The bare gold electrochemical sensor surface establishes a baseline impedance of an unmodified gold electrochemical sensor surface. A gold electrochemical sensor surface with ELP, but without thiol modified ELP, is designated "2" in FIG. 5. The small increase in impedance of 2 over 1 is believed to be attributed to non-specific physisorption of ELP to the gold electrochemical sensor surface. Physisorption, also known as physical absorption, refers to when an electronic structure of a molecule is barely perturbed upon absorption. A gold electrochemical sensor surface with thiol modified ELP is designated "3" in FIG. 5. The large increase in impedance of 3 over 1 and 2 is believed to be attributed to covalent attachment of ELP to the gold electrochemical sensor surface. While FIG. 5 illustrates results for a gold electrochemical sensor surface, one skilled in the art will appreciate that similar results may be obtained with other 2-dimensional metal and non-metal surfaces.

Figure 6:
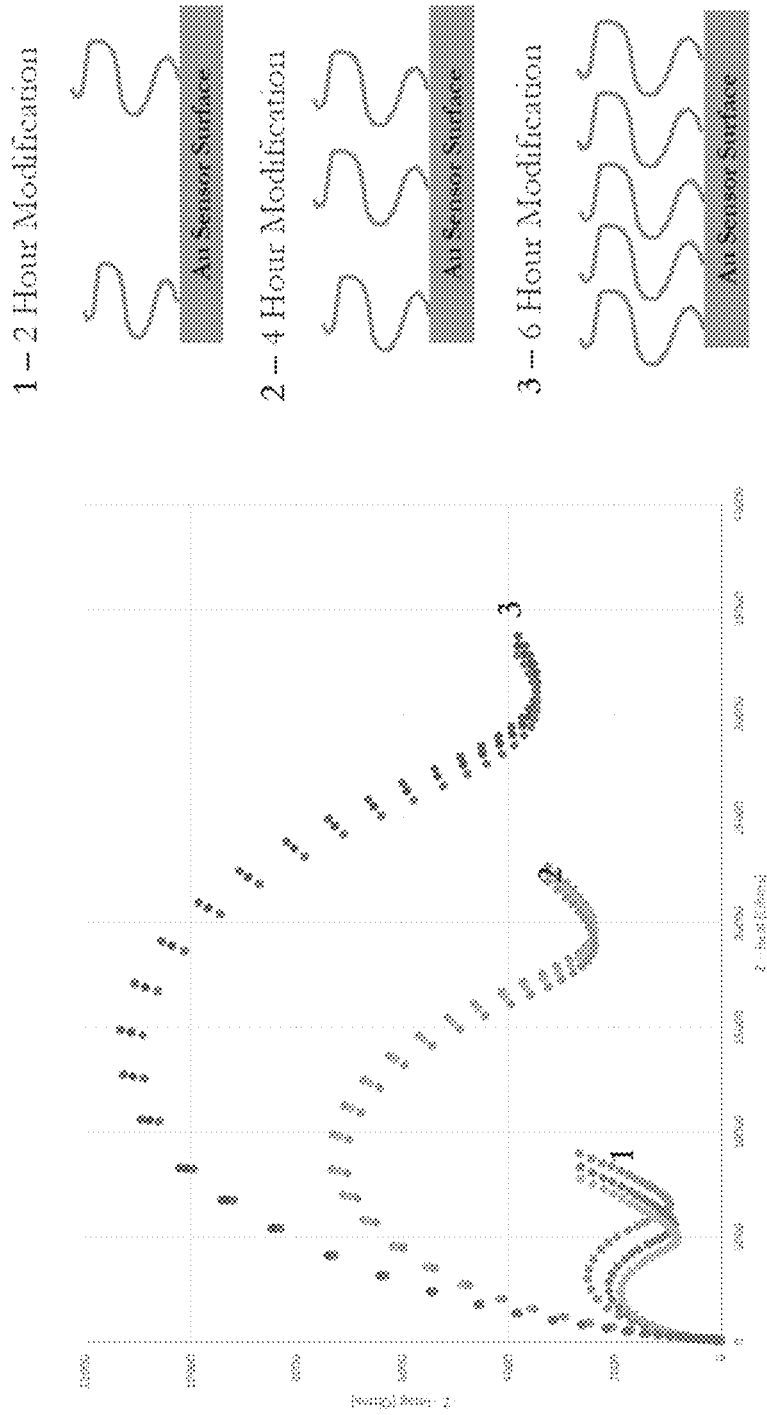
FIG. 6 is a Nyquist plot illustrating impedance of a gold electrochemical sensor surface after being contacted with a mixture of thiol-modified ELP for about 2 hours, a gold electrochemical sensor surface after being contacted with a mixture of thiol-modified ELP for about 4 hours, and a gold electrochemical sensor surface after being contacted with a mixture of thiol-modified ELP for about 6 hours.

FIG. 6 illustrates an attempt at optimizing surface modification to find a point where a 2-dimensional metal surface is covered in a uniform ELP monolayer. Contacting of a gold electrochemical sensor surface with a mixture of thiol-modified ELP for about 2 hours is designated "1" in FIG. 6. Contacting of a gold electrochemical sensor surface with a mixture of thiol-modified ELP for about 4 hours is designated "2" in FIG. 6. Contacting of a gold electrochemical sensor surface with a mixture of thiol-modified ELP for about 6 hours is designated "3" in FIG. 6. As FIG. 6 illustrates, observed impedance increased with the duration of contacting. While FIG. 6 illustrates results for a gold electrochemical sensor surface, one skilled in the art will appreciate that similar results may be obtained with other 2-dimensional metal and non-metal surfaces.

Figure 7:
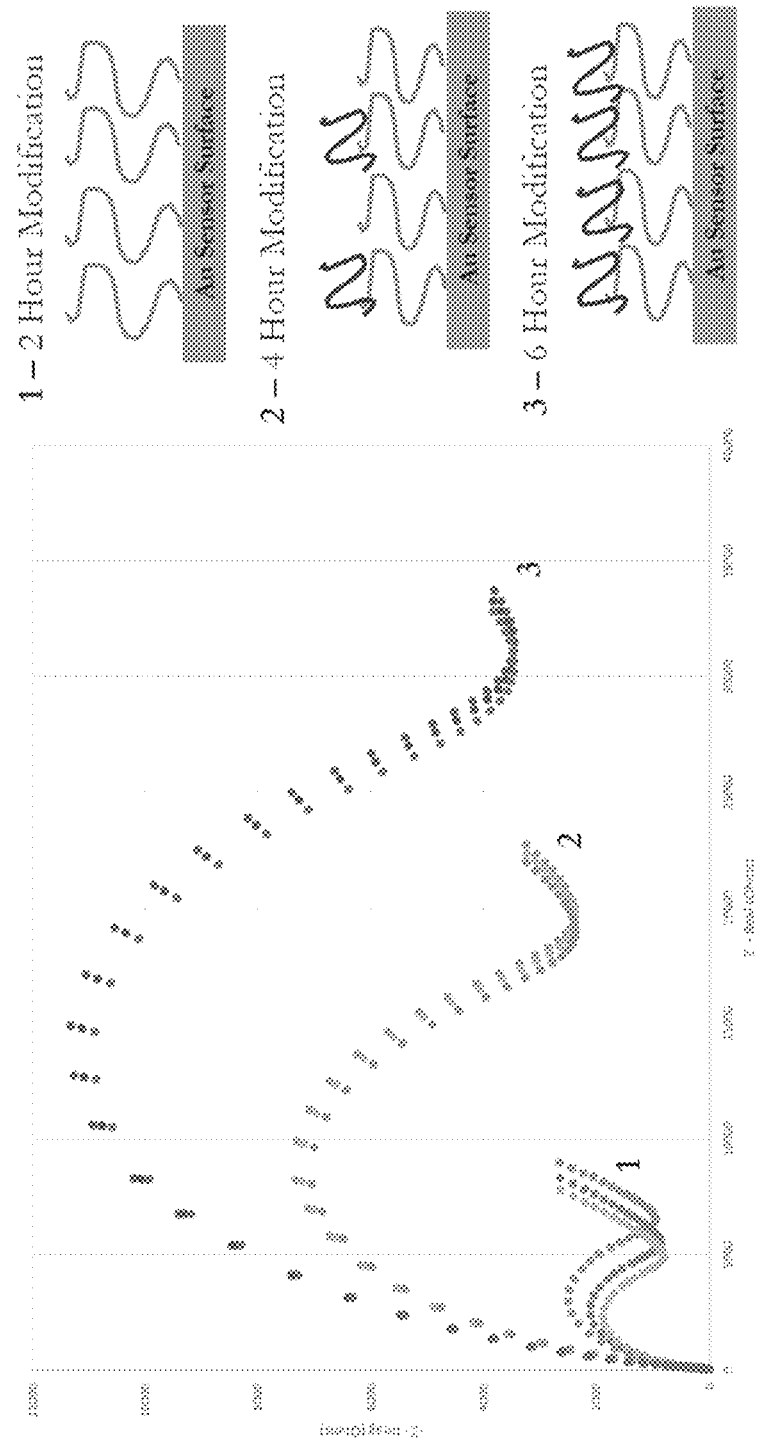
FIG. 7 is a Nyquist plot illustrating impedance of a gold electrochemical sensor surface after being contacted with a mixture of thiol-modified ELP for about 2 hours, a gold electrochemical sensor surface after being contacted with a mixture of thiol-modified ELP for about 4 hours, and a gold electrochemical sensor surface after being contacted with a mixture of thiol-modified ELP for about 6 hours.

The increased impedance illustrated in FIG. 6 was believed to indicate covalent binding of ELP to a gold electrochemical sensor surface increased as contact duration increased. However, subsequent testing (as illustrated in FIG. 7) demonstrated inconsistencies. This indicated, as illustrated in FIG. 7, that the measured increased impedance may not be due to increased covalent binding of ELP to the gold electrochemical sensor surface. Rather, the optimal covalent binding of ELP may occur after about 2 hours of contact, and the increased impedance measured thereafter may be attributed to non-covalent attachment of ELP to ELP already covalently attached to the gold electrochemical sensor surface.

Example 3

Removal of Physisorbed ELP from a 2-Dimensional Surface Modified with ELP

Means used to prepare ELPs such as, but not limited to: I40 ELPs and I40-Blocked ELPs for use these experiments are described in Example 1.

Figure 8:
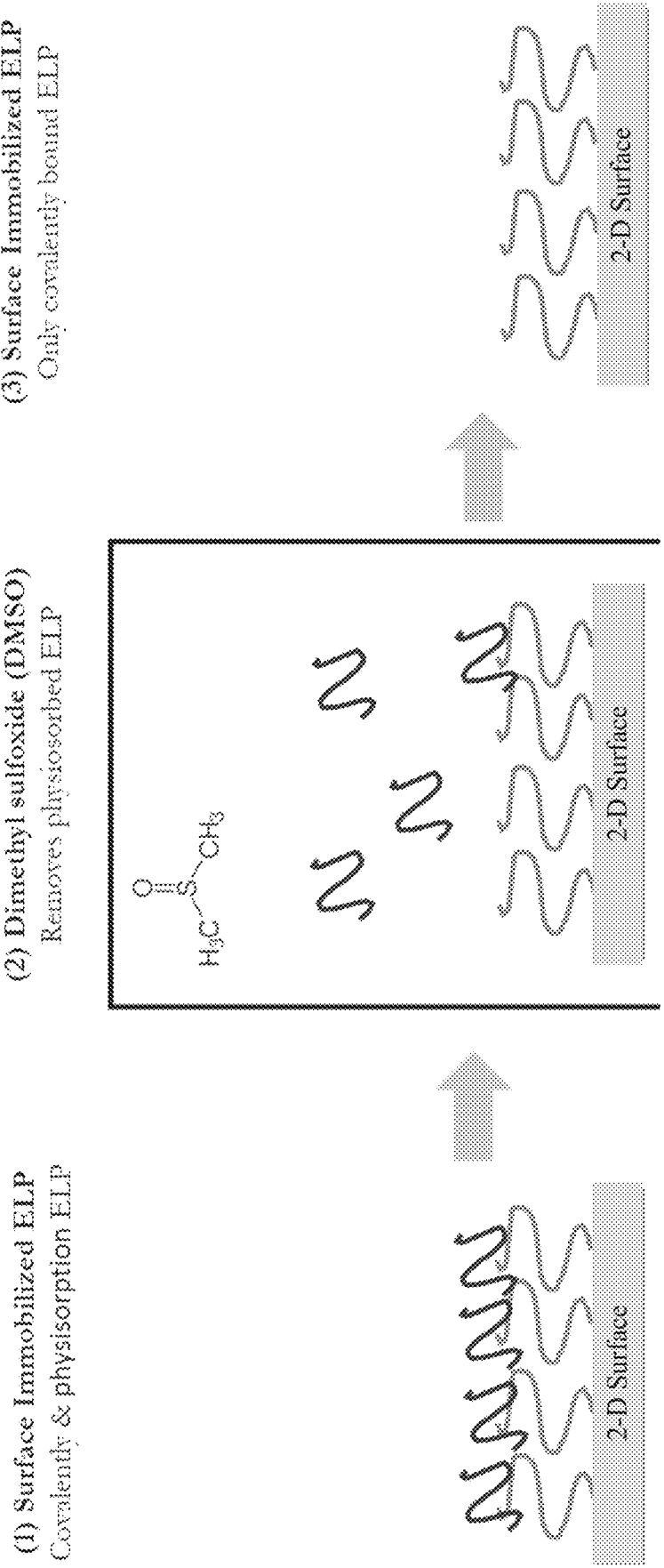
FIG. 8 is a conceptual diagram illustrating how physisorbed ELP may be removed from a 2-dimensional surface modified with ELP.

Physisorbed ELP may be removed from a 2-dimensional surface modified with ELP as illustrated in FIG. 8, in at least some embodiments of the present disclosure. The 2-dimensional surface modified with ELP and including physisorbed ELP may be contacted with (e.g., soaked in) dimethyl sulfoxide (DMSO). This is due, at least in part, to DMSO's ability to dissolve proteins. Use of DMSO was expected to transition from a 2-dimensional surface modified with ELP and including physisorbed ELP to a 2-dimensional surface with only covalently bound ELP.

Figure 9:
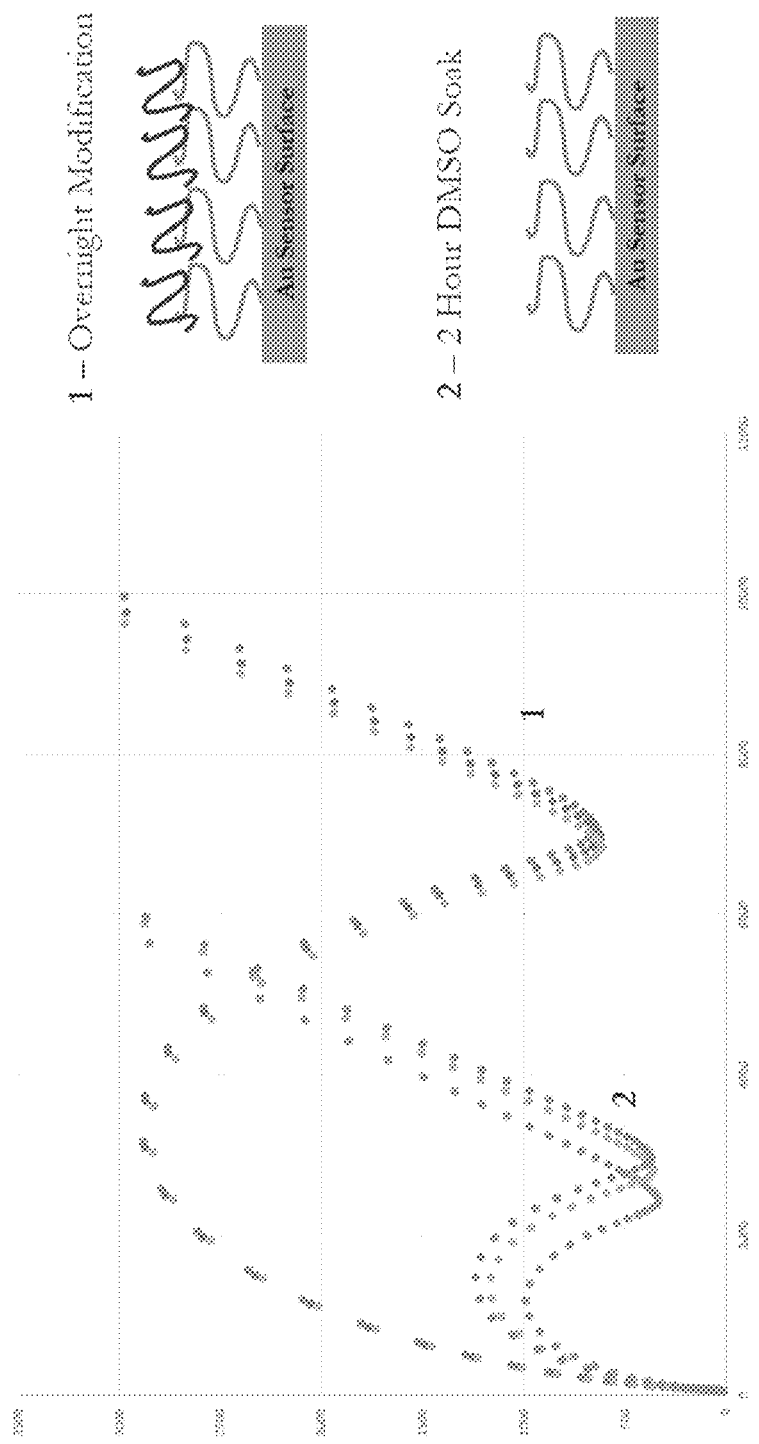
FIG. 9 is a Nyquist plot illustrating impedances attributed to removal of physisorbed ELP from a gold electrochemical sensor surface modified with covalently bound ELP.

FIG. 9 illustrates impedances attributed to removal of physisorbed ELP from a gold electrochemical sensor surface modified with covalently bound ELP according to certain embodiments of the present disclosure. A gold electrochemical sensor surface contacted, overnight, with a mixture of thiol-modified ELP is designated "1" in FIG. 9. "2" in FIG. 9 represents the gold electrochemical sensor surface of 1 after it was contacted with (e.g., soaked in) DMSO for about 2 hours. A decreased impedance was observed. Such decreased impedance indicated removal of physisorbed ELP from the surface bound ELP. While FIG. 9 illustrates results for a gold electrochemical sensor surface, one skilled in the art will appreciate that similar results may be achieved using other 2-dimensional metal and non-metal surfaces.

Figure 10:
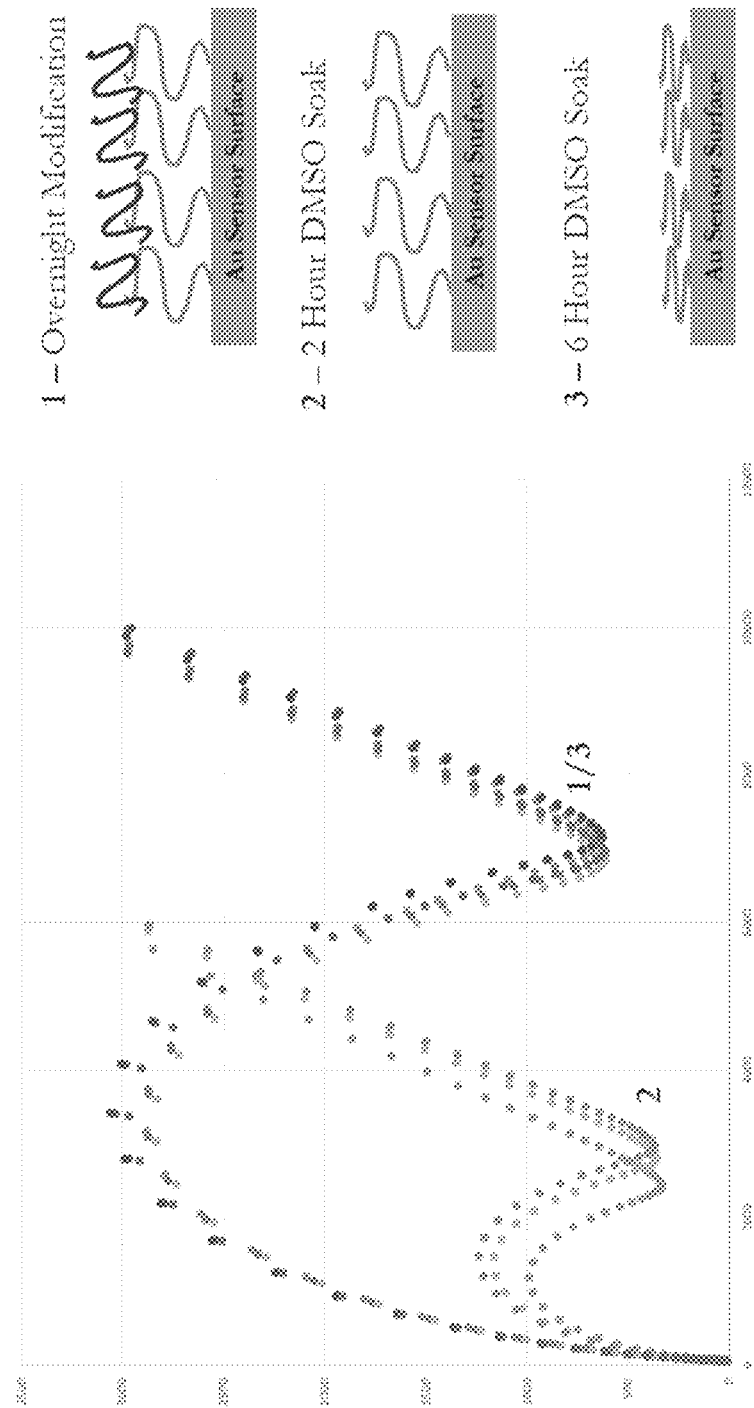
FIG. 10 is a Nyquist plot illustrating impedances measured for different durations of dimethyl sulfoxide (DMSO) contact with a gold electrochemical sensor surface modified with covalently bound ELP and including physisorbed ELP.

While increasing the duration of DMSO contact (e.g., soak) may be expected to result in a decreased impedance, an increased impedance was measured (as illustrated in FIG. 10). A gold electrochemical sensor surface contacted, overnight, with a mixture of thiol-modified ELP is designated "1" in FIG. 10. "2" in FIG. 10 represents the gold electrochemical sensor surface of 1 after it was contacted with (e.g., soaked in) DMSO for about 2 hours. "3" in FIG. 10 represents the gold electrochemical sensor surface of 1 after it was contacted with (e.g., soaked in) DMSO for about 6 hours. As illustrated in FIG. 10, the about 2 hour soak resulted in a decreased impedance while the about 6 hour soak resulted in an impedance similar to that measured for the surface pre-DMSO soak. Because no more ELP was introduced to the system, the increase impedance (from "2" to "3") was attributed to a conformational change of ELP on the surface where the DMSO is causing ELP to collapse on the surface to form a protein aggregate layer. While FIG. 10 illustrates results for a gold electrochemical sensor surface, one skilled in the art will appreciate that similar results may be obtained with other 2-dimensional metal and non-metal surfaces.

Figure 11:
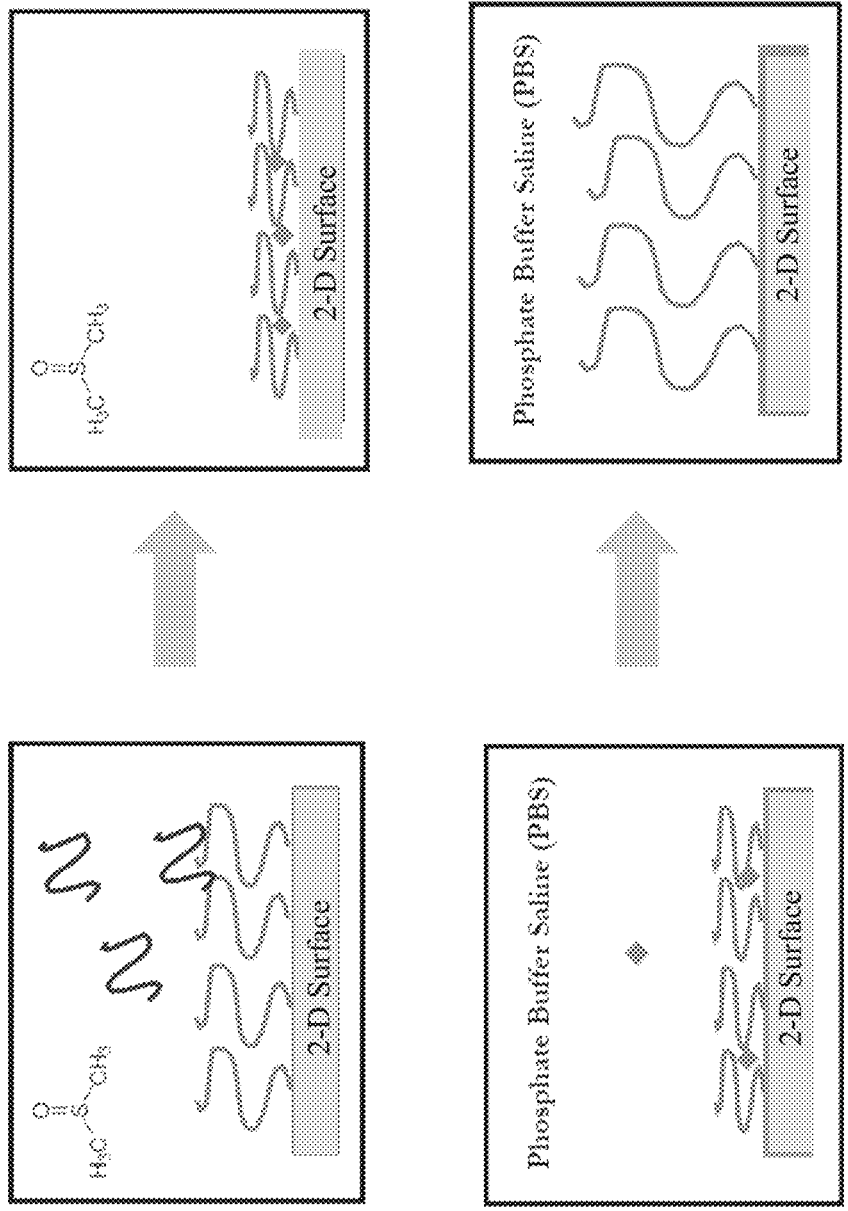
FIG. 11 is a schematic diagram illustrating how DMSO may cause a conformational change of ELP and how such effect may be reversed.

Based on the experiment represented in FIG. 10, it was hypothesized that DMSO first removed physisorbed ELP (as illustrated by the top left box in FIG. 11) and then saturated ELP convalently bound to a 2-dimensional surface, causing a conformational change of the ELP, in turn causing the ELP to collapse (represented in the top right box of FIG. 11) to trap DMSO (represented as diamonds in the top right box of FIG. 11) within the core of the ELP. To passivate this effect, the 2-dimensional surface with the collapsed ELP (illustrated in the top right box of FIG. 11) was contacted with (e.g., soaked in) phosphate buffer saline (PBS) (as illustrated by the bottom left box of FIG. 11). In at least some embodiments, such contacting may occur at about 4° C. Results indicated the process caused the ELP to release the DMSO into solution and re-extend from the 2-dimensional surface (as illustrated by a transition from the bottom left box to the bottom right box of FIG. 11).

Figure 12:
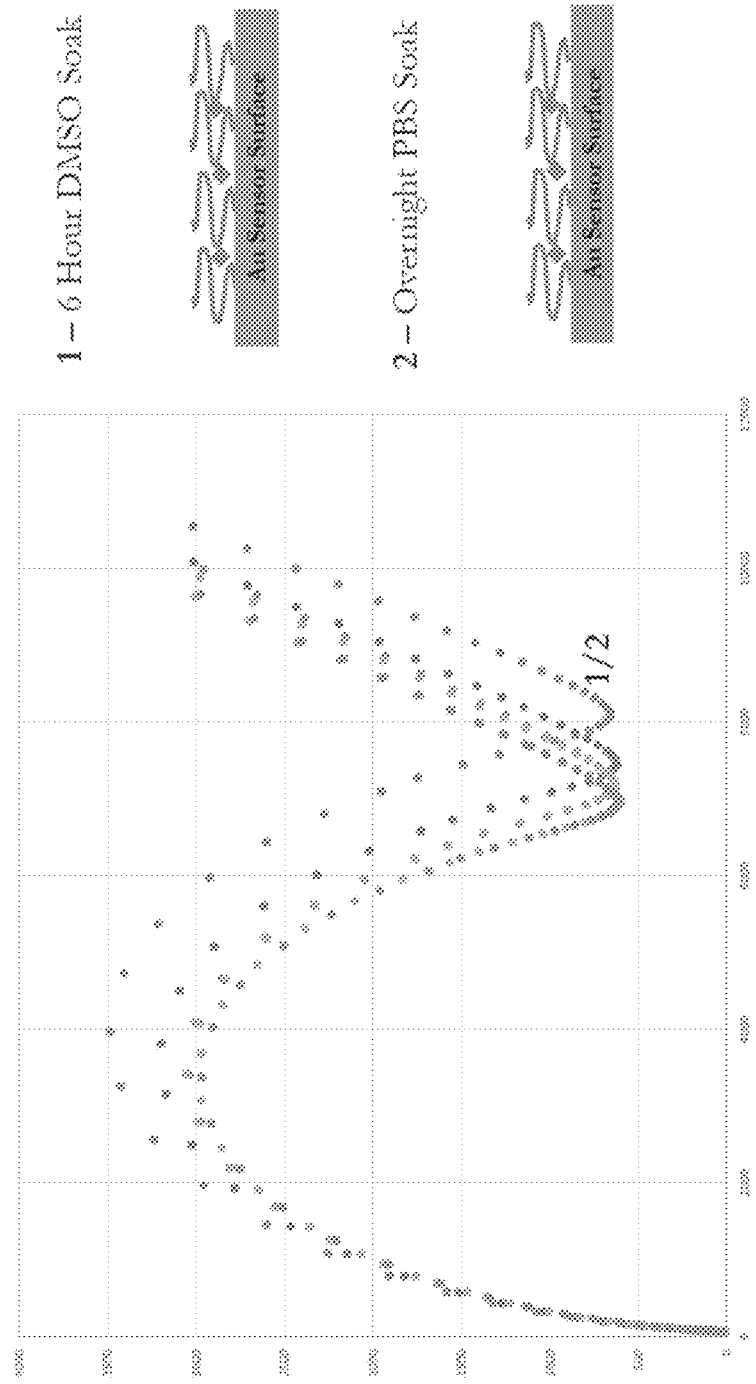
FIG. 12 is a Nyquist plot illustrating impedances measured for a gold electrochemical sensor surface pre- and post-phosphate buffer saline (PBS) contact.

FIG. 12 illustrates measured impedances for a gold electrochemical sensor surface pre- and post-PBS contact. The gold electrochemical sensor surface may be contacted with (e.g. soaked in) PBS in a vacuum oven. A gold electrochemical sensor surface modified with ELP and contacted with (e.g., soaked in) DMSO for about 6 hours is designated "1" in FIG. 12. The gold electrochemical sensor surface was thereafter contacted with (e.g., soaked in) PBS overnight at about 4° C. (designated as "2" in FIG. 12). As illustrated in FIG. 12, no change in impedance was measured. This indicated the ELP did not release DMSO, confirming a non-reversible conformation change of surface bound ELP in the presence of DMSO. While FIG. 12 illustrates results for a gold electrochemical sensor surface, one skilled in the art will appreciate that similar results may be obtained with other 2-dimensional metal and non-metal surfaces.

Example 4

Impedance Response Assessments

Studies were performed to assess impedance responses of unmodified, I40 modified, and I40-Blocked modified electrodes. The impedance data was graphed using a Nyquist plot of the imaginary impedance vs real impedance. A Randle's circuit with a constant phase element was used to interpret the impedance data by calculating the charge transfer resistance and other components of the impedance response. Charge transfer resistance (Rct), a component of impedance, was used to compare the impedance response of unmodified, I40 modified, and I40-Blocked modified electrodes. Charge transfer resistance (Rct) is correlated to the diameter of the semi-circular region of the Nyquist curve; larger diameters represent higher charge transfer resistance values.

Figure 15:
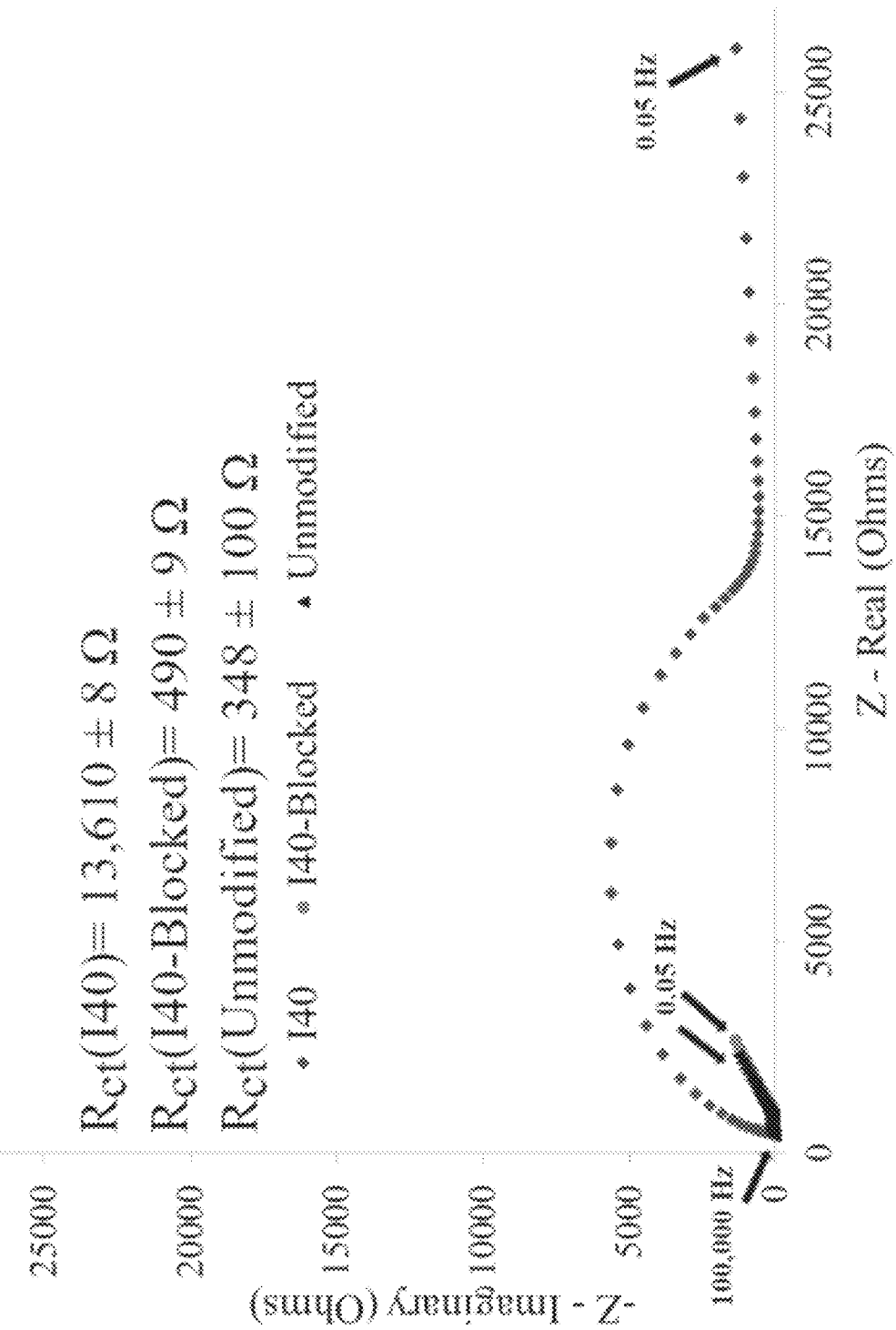
FIG. 15 illustrates impedance response showing a significant increase in charge transfer resistance for an I40 modified electrode, which is absent on an I40-Blocked modified electrode. Results from an unmodified electrode are also shown. The increase in charge transfer resistance indicates a strong attachment of I40 to the electrode surface. Traces shown for I40 (diamond), I40-Blocked (circle); and unmodified (triangle).

An increase in charge transfer resistance was expected after gold electrode modification resulting from the insulating layer formed by the polymer on the electrode surface hindering the kinetics of the redox couple exchange. The impedance response for an unmodified electrode was compared to that of an electrode modified with either I40 or I40-Blocked (see FIG. 15). Charge transfer resistance values for each electrode were included in FIG. 15.

Figure 16:
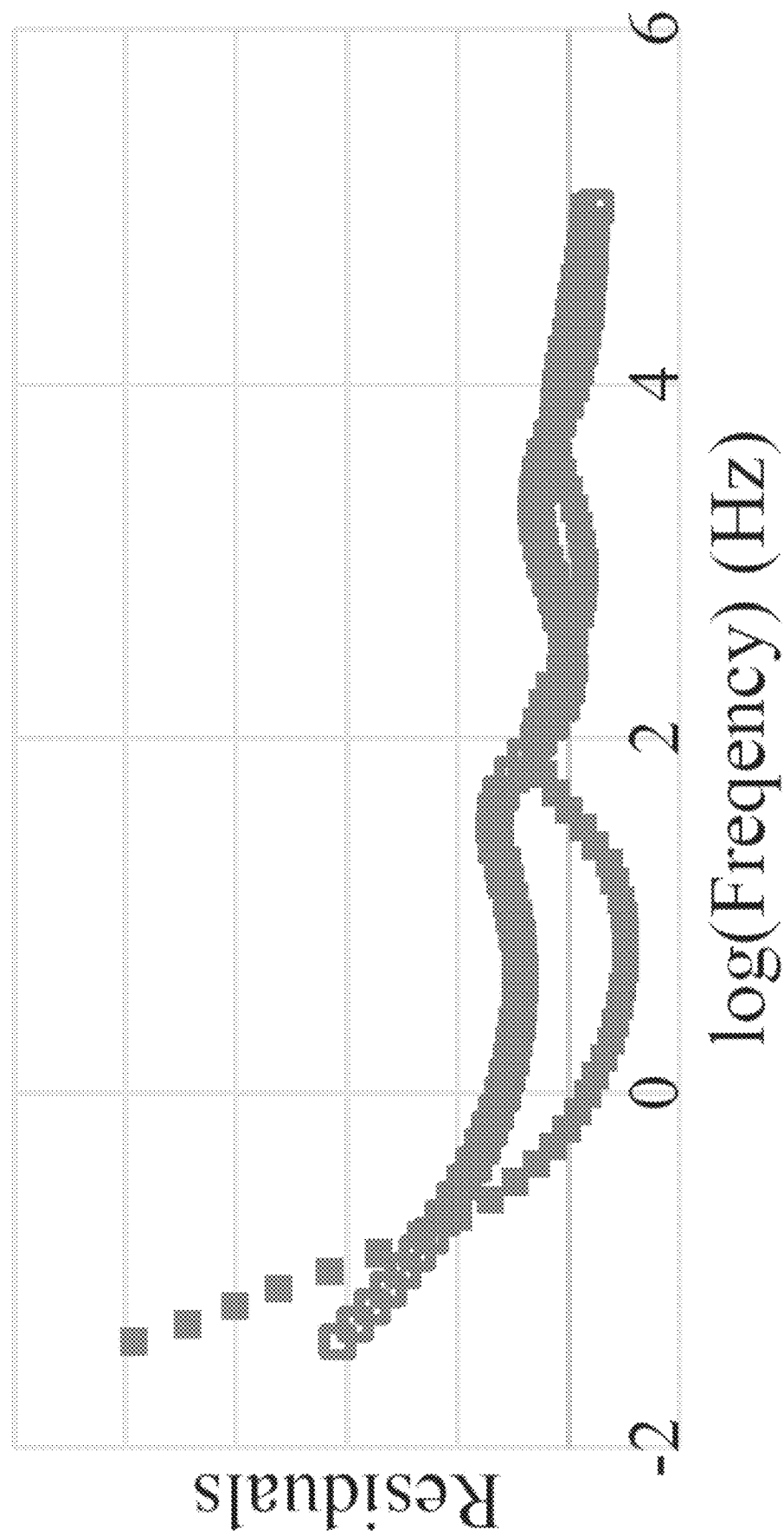
FIG. 16 is a residual fractional error curve evaluating quality of fit for an I40 modified electrode.
Figure 17:
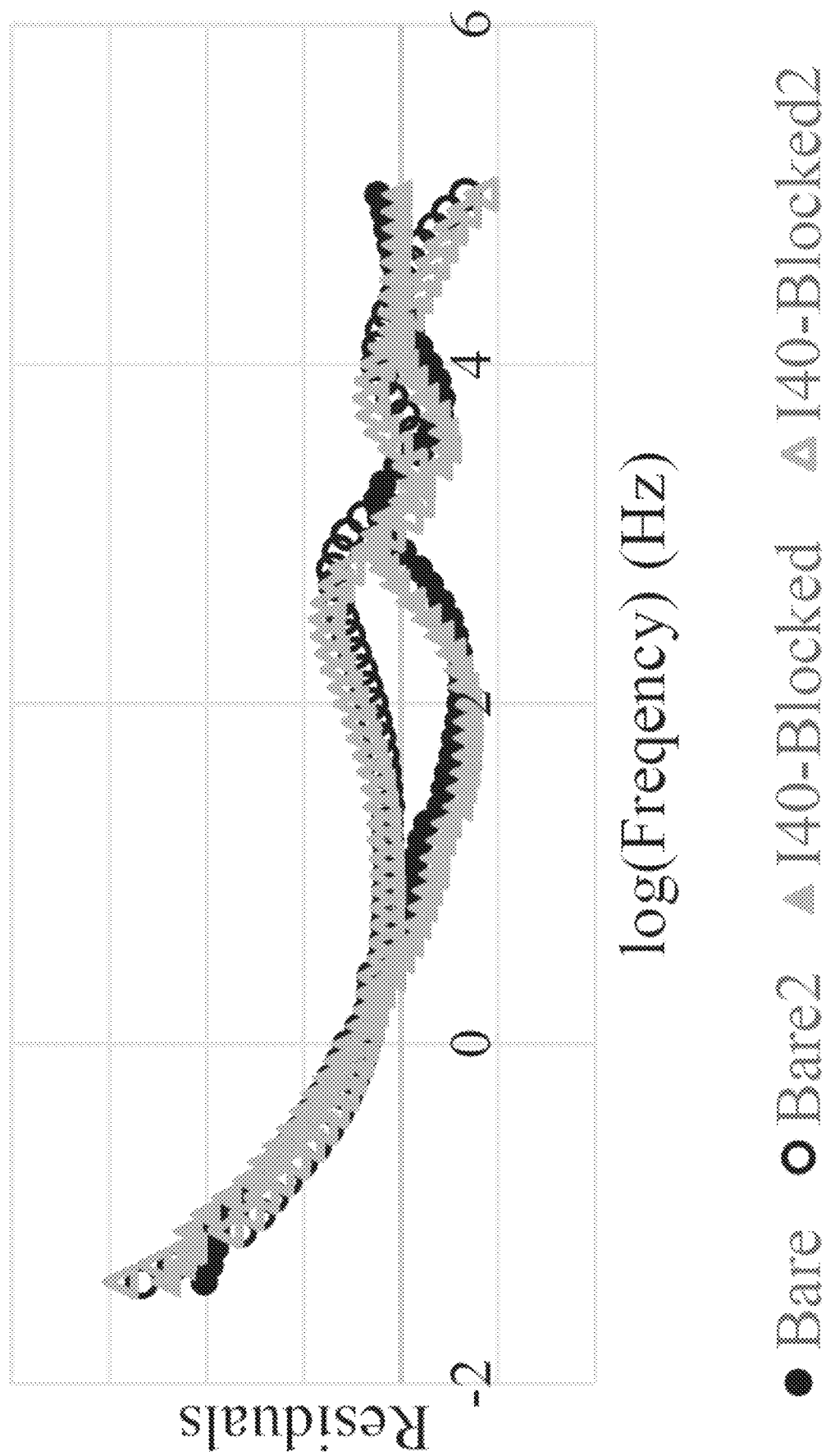
FIG. 17 is a residual fractional error curve evaluating quality of fit for a bare (unmodified) electrode and an I40-Blocked modified electrode. The graph shows data from two experiments, with results for one experiment shown with closed circles (Bare) and triangles (I40-Blocked), and results of the second shown in open circles Bare 2) and triangles (I40-Blocked2).

FIGS. 16 and 17 show residual fractional error curves evaluating the quality of fit of the Randle's circuit model to the impedance data. All fits (I40, I40-Blocked, and unmodified) show even distribution over the frequency range with lack of major trends, indicating the Randle's circuit model is appropriate to fit the data.

The impedance response of an unmodified electrode showed minimal charge transfer resistance with a Warburg impedance tail extending at about 45° observed on the Nyquist plot, indicating semi-infinite diffusion of the redox couple to the electrode surface unrestricted by any surface features. The observed impedance response of the unmodified electrode can be described as a purely mass transfer limited process.

For an I40 modified electrode, there was a significant increase in charge transfer resistance of 13,262Ω compared to an unmodified gold electrode, shown graphically by the increase in semi-circle diameter of the Nyquist plot. The increase in charge transfer resistance on the I40 modified electrode compared to an unmodified electrode was caused by the formation of an insulating layer on the electrode surface validating the presence of I40 on the electrode after modification.

The impedance response of an I40-Blocked modified electrode was almost identical to that of an unmodified gold electrode. A small increase in charge transfer resistance of 142Ω was observed, possibly attributable to a minor degree of non-specific physisorption between the polymer and electrode surface. However, compared to the response of an I40 modified electrode, the increase in charge transfer resistance was insignificant. Additionally, the large difference in charge transfer resistance between the I40 and I40-Blocked modified electrode indicated the polymers interacted differently with the gold electrode surface. Because I40 and I40-Blocked differed only in the presence of a modified cysteine residue, the difference in polymer affinity to the electrode surface was largely determined by the thiol-accessibility, as opposed to non-specific interactions. This validated I40 surface attachment minimized physisorption of the polymer to the electrode surface.

Example 5

Further Validation of ELP Gold Surface Modification

Figure 18B:
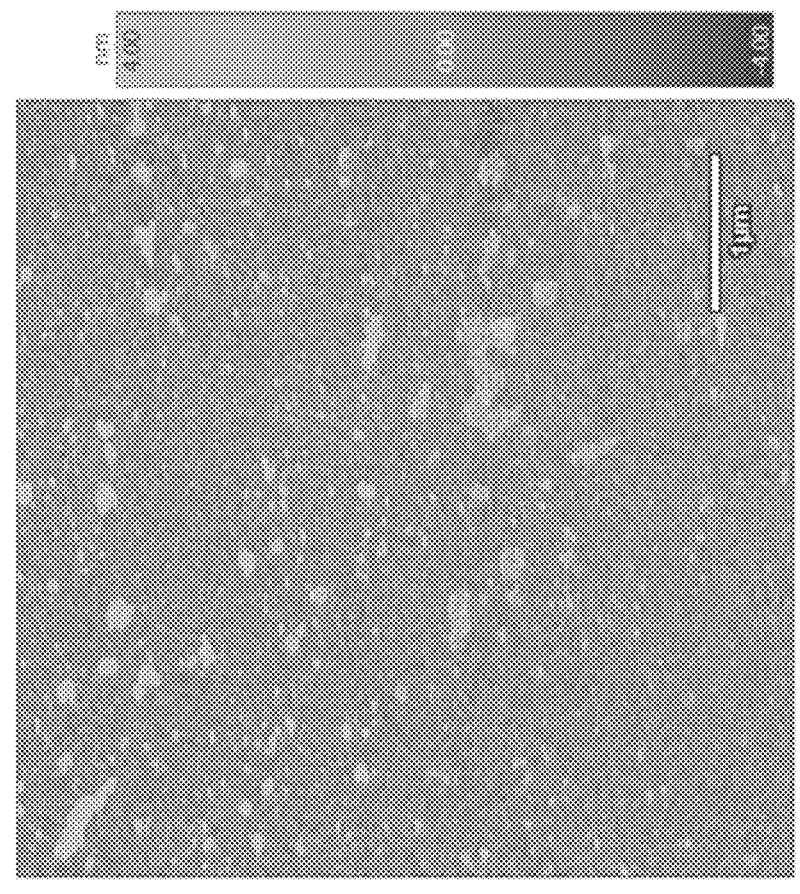
FIG. 18B is an AFM height image of a gold surface modified with I40. The AFM height image was imaged in water and shows surface features over 4.0 nm in height.
Figure 18A:
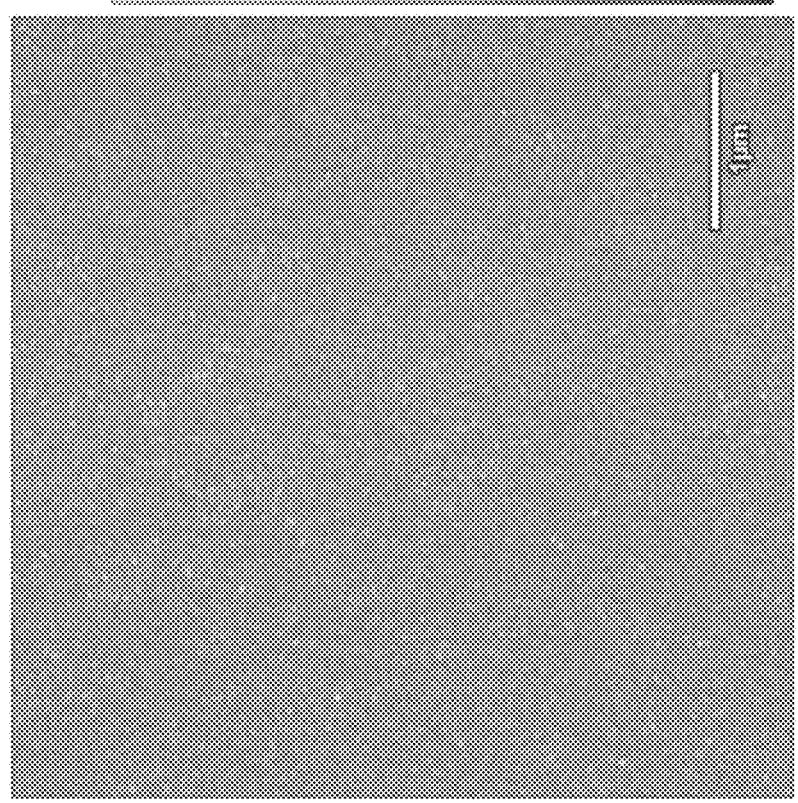
FIG. 18A is an atomic force microscopy (AFM) height image of an unmodified gold surface. The AFM height image was imaged in water and shows the absence of surface features.

Atomic Force Microscopy (AFM) was used to characterize the I40 gold surface modifications. See Example 1 for additional AFM method information). In these studies, further validation of the I40 gold surface modification was achieved by comparing the surface topography of an unmodified gold surface to a gold surface modified with I40 imaged using AFM in liquid (see FIGS. 18A and 18B).

After modification with I40, numerous surface features over 4.0 nm in height were present, forming a partial layer on the gold surface. Comparatively, the unmodified gold surface was more uniform and lacked similar surface features over 4.0 nm in height, consistent with the Warburg impedance dominate response of an unmodified electrode. Particle analysis of surface features over 4.0 nm in height on the I40 modified gold surface revealed a particle surface area of 1.22 µm$^2$ corresponding to a 4.88% total surface coverage in the region sampled. For sensor applications, low surface area coverage can be beneficial in reducing steric hindrances and interactions between adjacent polymers, helping to ensure a reproducible response. The detection of surface features on the I40 modified gold surface, absent on the unmodified gold surface, is consistent with the hypothesis that the I40 interaction with the gold electrode surface is the cause of the charge transfer resistance increase after modification.

Example 6

Reproducibility of the I40 Gold Electrode Modification

Studies were performed to evaluate the reproducibility of gold electrode surface modifications. Reproducibility is important for a consistent and reliable response in subsequent characterization steps. Reproducibility of the I40 surface modification was evaluated by comparing the impedance response across multiple unique modification events (N=6) (see FIG. 19). An average charge transfer resistance of 12.7±1.4 kOhms was reported, demonstrating sufficient agreement in the impedance response observed across the different electrodes. Agreement in the impedance responses obtained across the different electrodes indicated consistent electrode coverage by the I40 layer formed on the surface from each unique modification event. Calculated charge transfer resistance values for each electrode in FIG. 19 are included in the following Table 1:

TABLE 1

Figure 19:
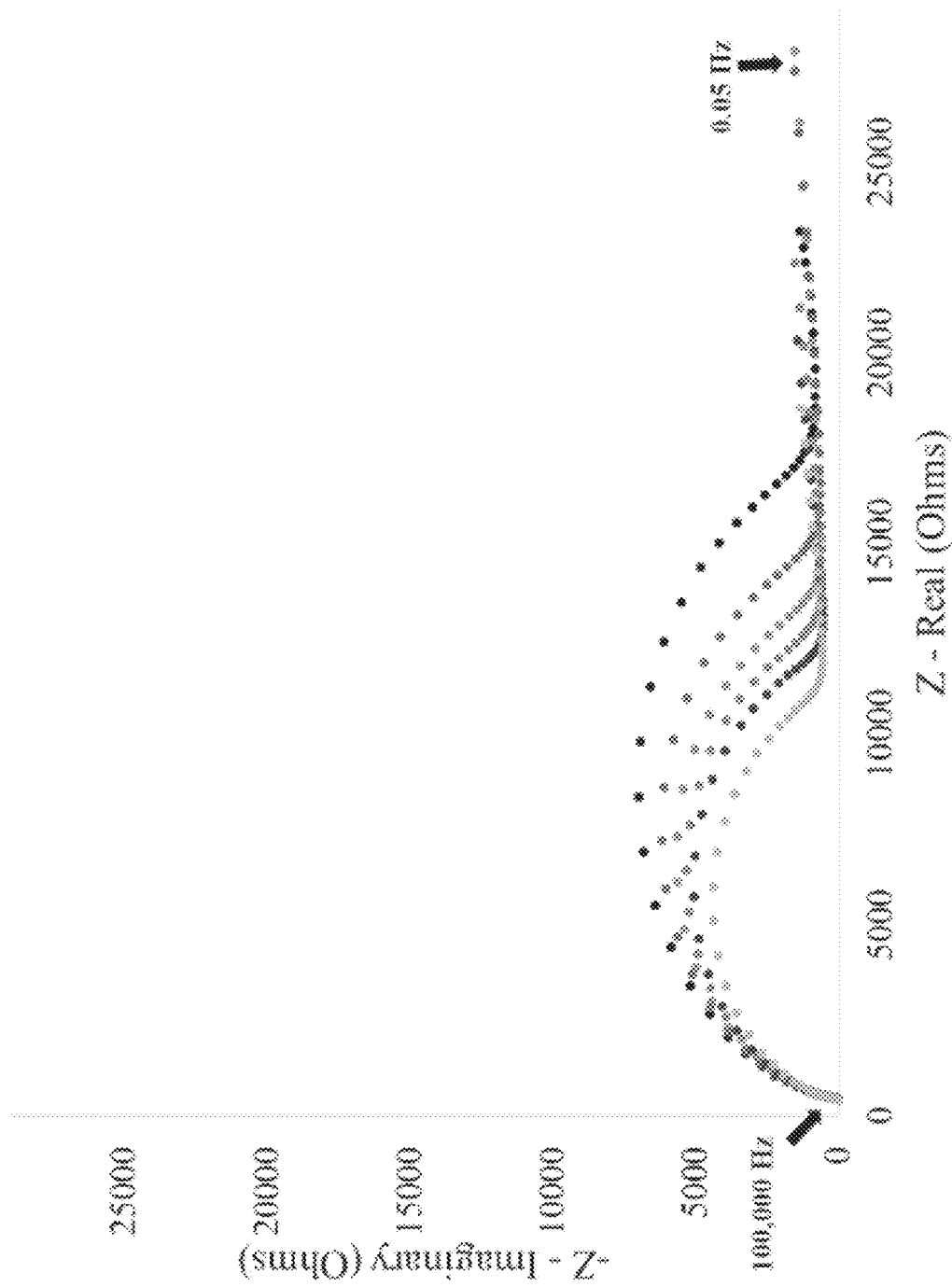
FIG. 19 illustrates impedance response from six unique modification events with I40 with an average charge transfer resistance of 12.7±1.4 kOhms. See Table 1 for additional information)

Charge transfer resistance values for each electrode in FIG. 19.

| | $R_{ct}$ (Ohms) |
| --- | --- |
| Electrode 1 | 17.13 × 10$^3$ ± 132.3 |
| Electrode 2 | 13.61 × 10$^3$ ± 105.2 |
| Electrode 3 | 14.96 × 10$^3$ ± 115.4 |
| Electrode 4 | 11.98 × 10$^3$ ± 89.91 |
| Electrode 5 | 12.75 × 10$^3$ ± 98.27 |
| Electrode 6 | 10.99 × 10$^3$ ± 84.37 |

Example 7

Stimuli Response Characterization

Having achieved a reproducible I40 surface modification, the stimuli-response was characterized by exposing surface-immobilized I40 to varying molarities of sodium chloride (NaCl) salt and recording the impedance response. Exposing an I40 modified electrode to a high salt environment was expected to result in I40 collapse, reducing the available electrode surface area and decreasing the available diffusion pathways to hinder the kinetics of the redox couple exchange, resulting in an increase in charge transfer resistance.

Figure 20:
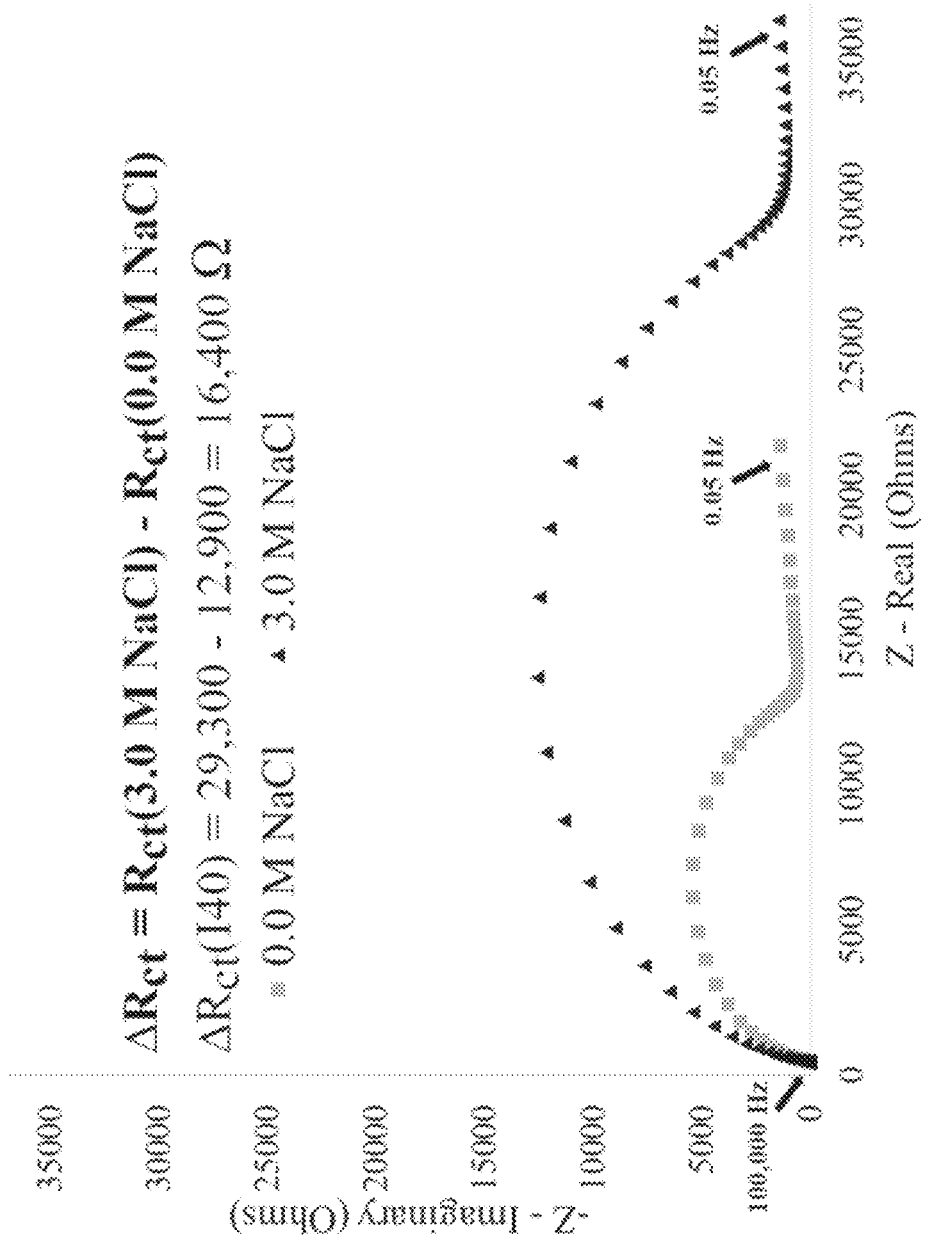
FIG. 20 shows impedance spectra for an I40 modified electrode with a 16,400Ω increase in charge transfer resistance from 0.0 M NaCl to 3.0 M NaCl, showing stimuli-response.

An increase in charge transfer resistance of 16,400Ω was observed after exposing an I40 modified electrode to a high salt environment (see FIG. 20). At the low salt concentration, a lower charge transfer resistance was observed consistent with the extended state of the I40. The low salt concentration would decrease intramolecular interactions of the surface-immobilized I40, allowing for greater accessibility of the electrode surface to the redox couple exchange. Charge transfer resistance increased after exposure to a high salt environment, indicting an increase in the insulating layer on the electrode surface. This is consistent with the hypothesis that surface-immobilized I40 undergoes collapse, leading to a reduction in available diffusion pathways and/or electrode surface area for redox couple exchange and hindering the kinetics of the reaction.

Figure 21:
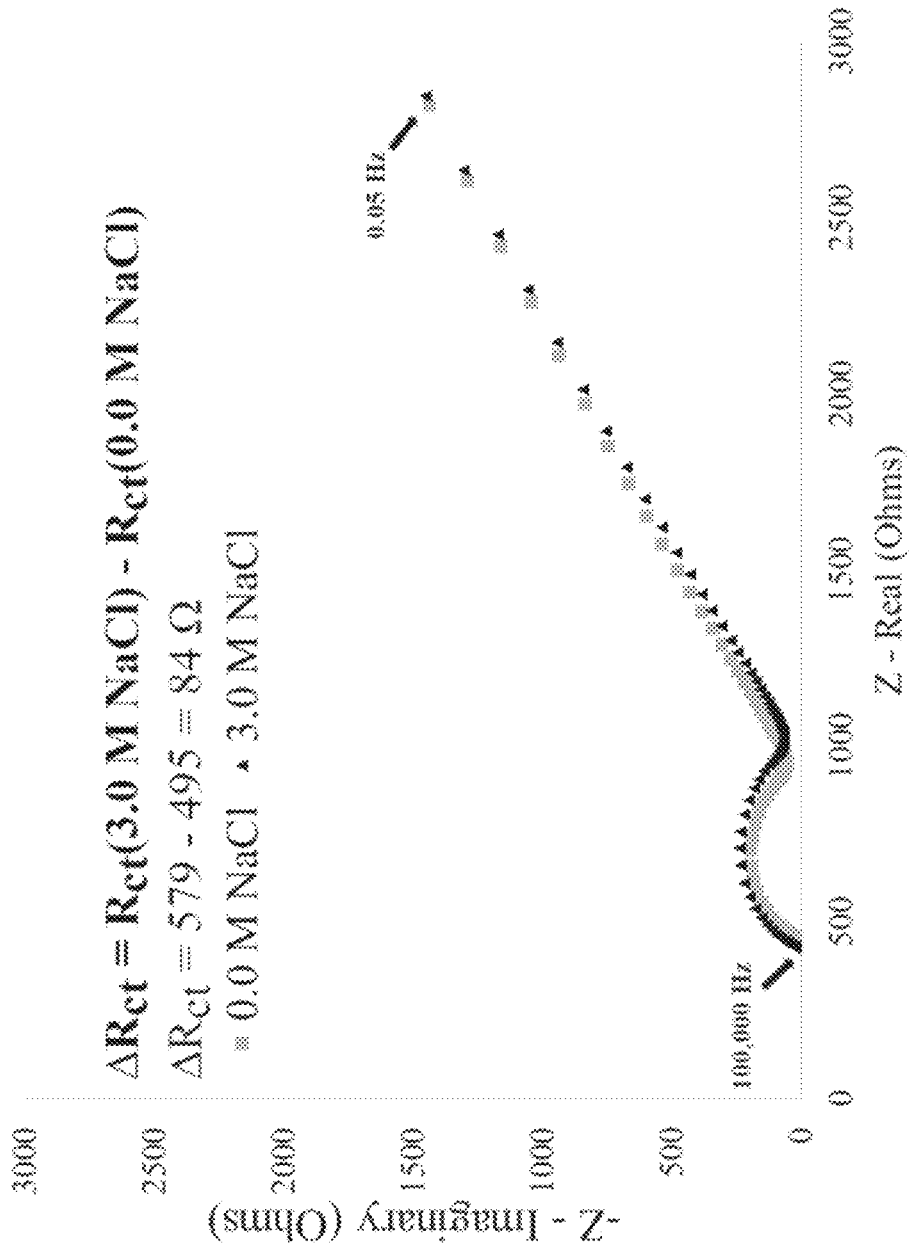
FIG. 21 shows impedance spectra for an I40-Blocked modified electrode with an 84Ω increase in charge transfer resistance from 0.0 M NaCl to 3.0 M NaCl, showing lack of stimuli-response.

For an I40-Blocked modified electrode, an increase in charge transfer resistance of 84Ω was observed after exposure to a high salt environment, indicting insignificant changes at the electrode surface (see FIG. 21). This supports the hypothesis that the observed changes in charge transfer resistance from an I40 modified electrode can be attributed to the stimuli-responsive behavior of I40 immobilized by a strong cysteine-gold attachment.

Figure 22:
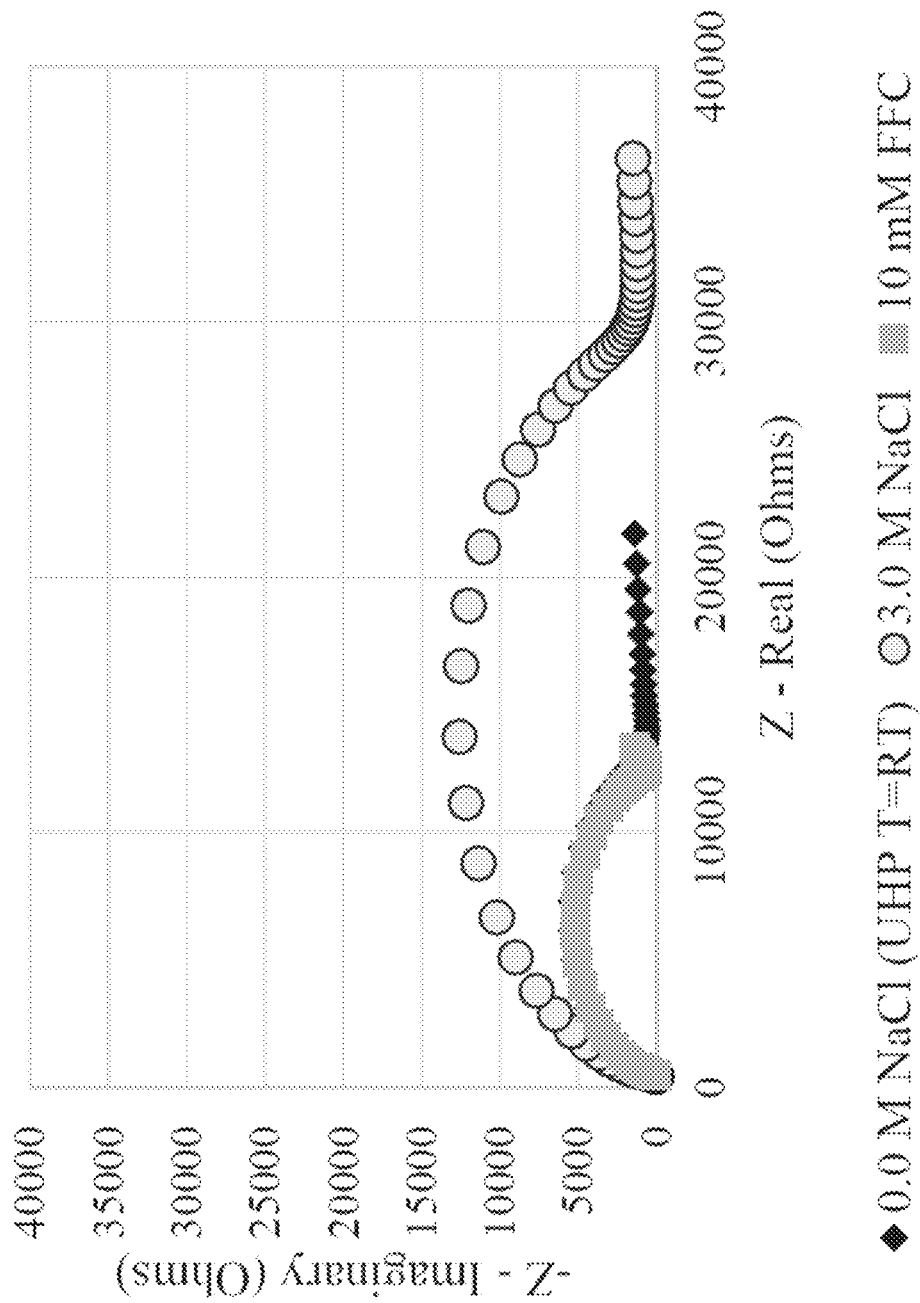
FIG. 22 shows impedance spectra obtained after soaking an I40 modified electrode in redox couple solution.

To measure the impedance response, the modified electrode was transferred from the experimental condition into a 10 mM [Fe(CN)$_6$]$^{3-/4-}$ redox couple solution, a low molarity salt solution. To ensure the molarity of the redox couple solution did not influence the stimuli-response, the impedance response was recorded after exposing an I40 modified electrode to the 10 mM $[Fe(CN)_6]^{3-/4-}$ overnight. After exposure to the 10 mM $[Fe(CN)_6]^{3-/4-}$ the impedance response from an I40 modified electrode agreed with the impedance response from the 0.0 M NaCl condition, indicating the molarity of the redox couple solution is sufficiently low not to significantly influence the morphological changes associated with the stimuli-response of surface-immobilized I40 for the time needed to measure the impedance response (about 10 minutes). FIG. 22 is a Nyquist plot obtained from the foregoing experiment.

Example 8

Reversibility of Stimuli-Response

Figure 23:
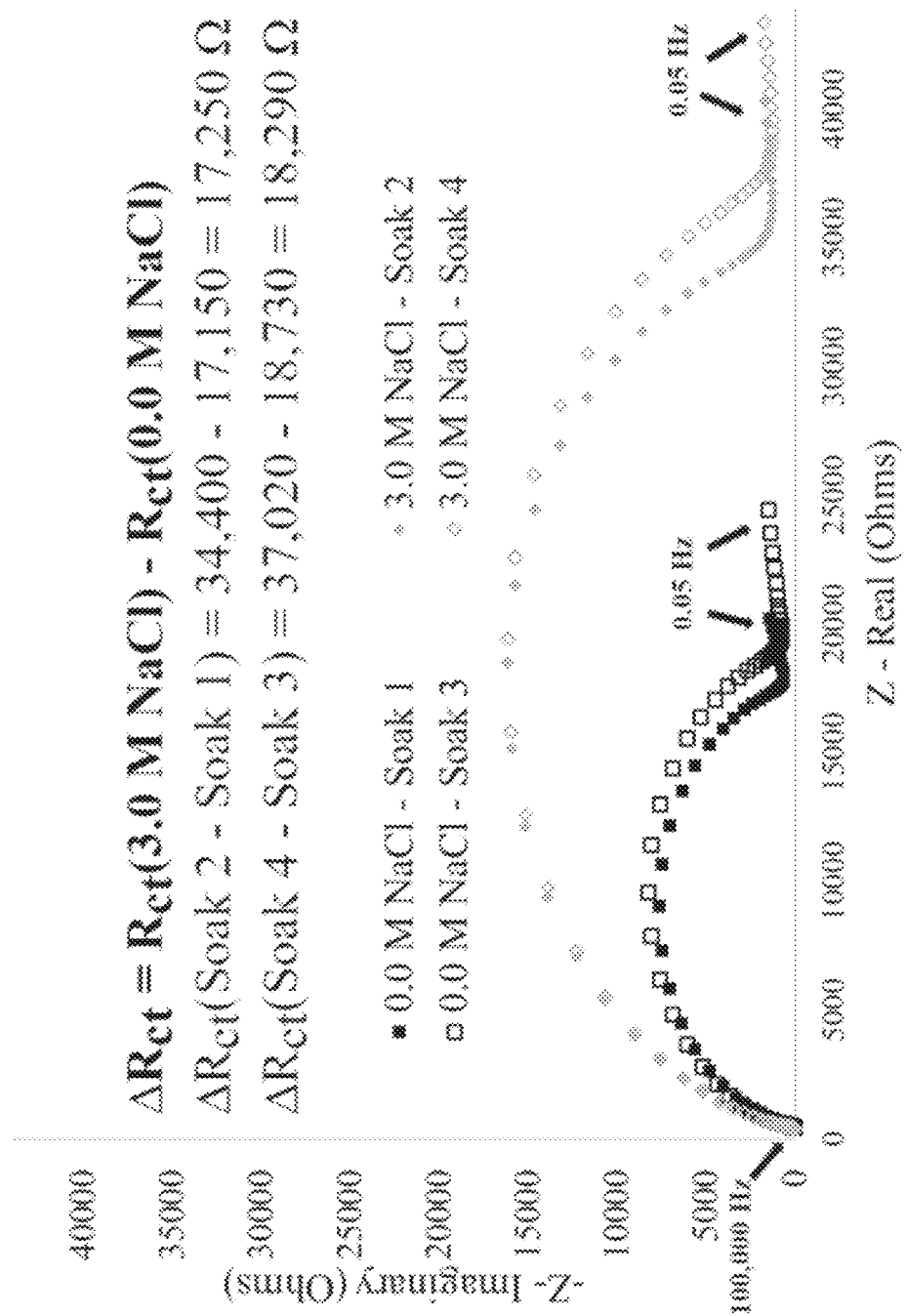
FIG. 23 shows impedance spectra of an I40 modified gold electrode after exposures to 0.0 M NaCl or 3.0 M NaCl, showing agreement in charge transfer resistance and demonstrating stimuli-response reversibility.

The reversibility of the stimuli-response was evaluated by comparing the impedance response from an I40 modified electrode after multiple exposures to low salt or high salt concentration environments (see FIG. 23). Reversibility of the stimuli-response was demonstrated by the respective increase or decrease in charge transfer resistance after exposure to high salt or low salt concentration environments, respectively, consistent with the extension and collapse model described herein. Additionally, the change in magnitude of charge transfer resistance was nearly identical for the transition from low salt to high salt concentrations (17,250Ω) as it was for the reverse, high salt to low salt concentrations (18,730Ω), indicating the direction of the stimulus change does not influence the magnitude of response. The reversibility of the stimuli-response showed potential in reusable systems. Since the stimuli-response can be reversed, a single modified surface can be reused for multiple unique events, an important feature for development of low-cost technologies.

Example 9

Stimuli Response with Varying Sodium Chloride Molarities

Figure 24:
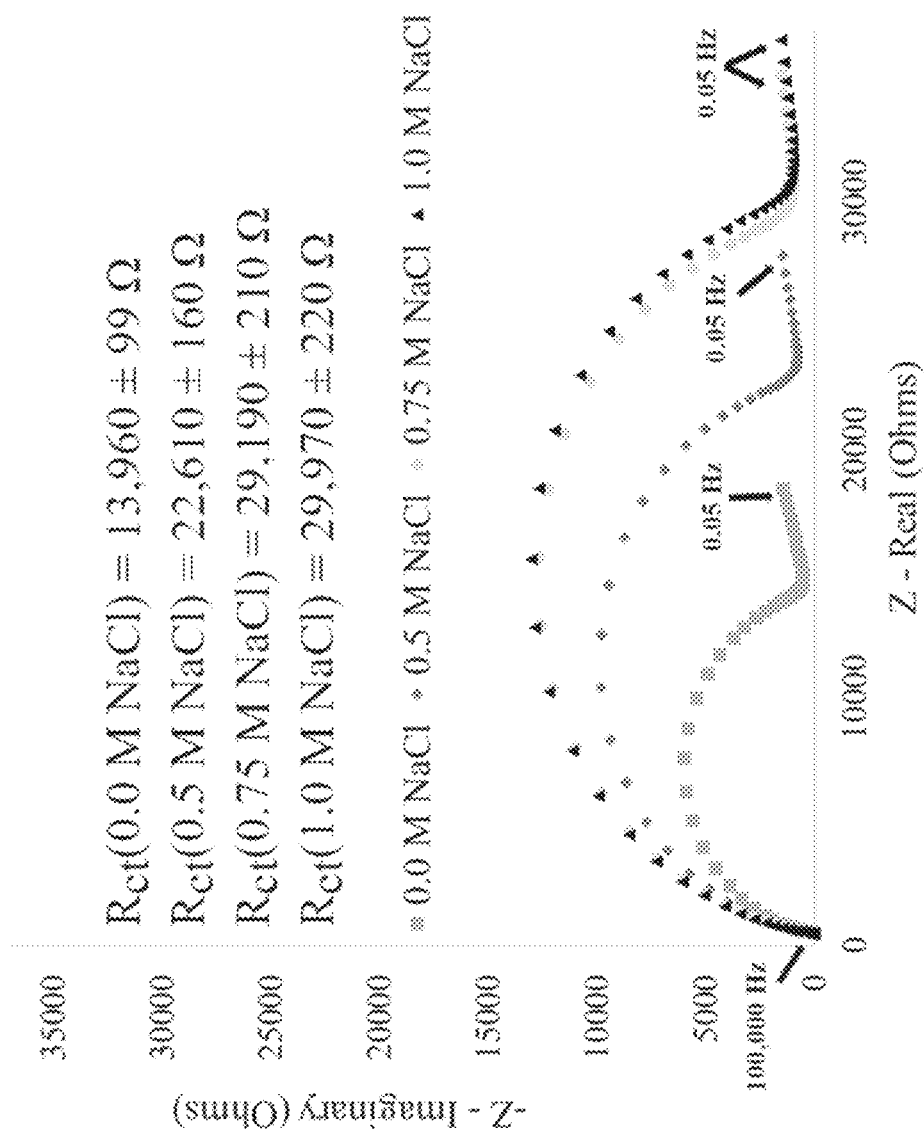
FIG. 24 shows impedance spectra of an I40 modified electrode, showing increasing saturation in the stimuli-response with an intermediate state between the maxima and minima.

The stimuli-response of surface-immobilized I40 was further characterized by exposing an I40 modified electrode to varying molarities of sodium chloride (NaCl) (see FIG. 24). The impedance response from an I40 modified electrode showed an increase in charge transfer resistance with increasing NaCl concentration. After exposure to the 0.0 M NaCl environment, the modified electrode had the lowest charge transfer resistance, consistent with the hypothesis of the extended state at low salt concentrations. Exposing the modified electrode to increasing molarities of sodium chloride showed an initial increase in charge transfer resistance at 0.5 M NaCl with a saturation in the response after exposure to 0.75 M NaCl and 1.0 M NaCl. Agreement in the charge transfer resistance values for 0.75 M NaCl and 1.0 M NaCl concentrations indicate the stimuli-response has been saturated, resulting in a structure that is no longer dynamic. Additionally, the impedance response from the 0.5 M NaCl condition fell between the maxima and minima for charge transfer resistance, providing evidence of intermediate states existing between the extended and collapsed states.

Figure 25:
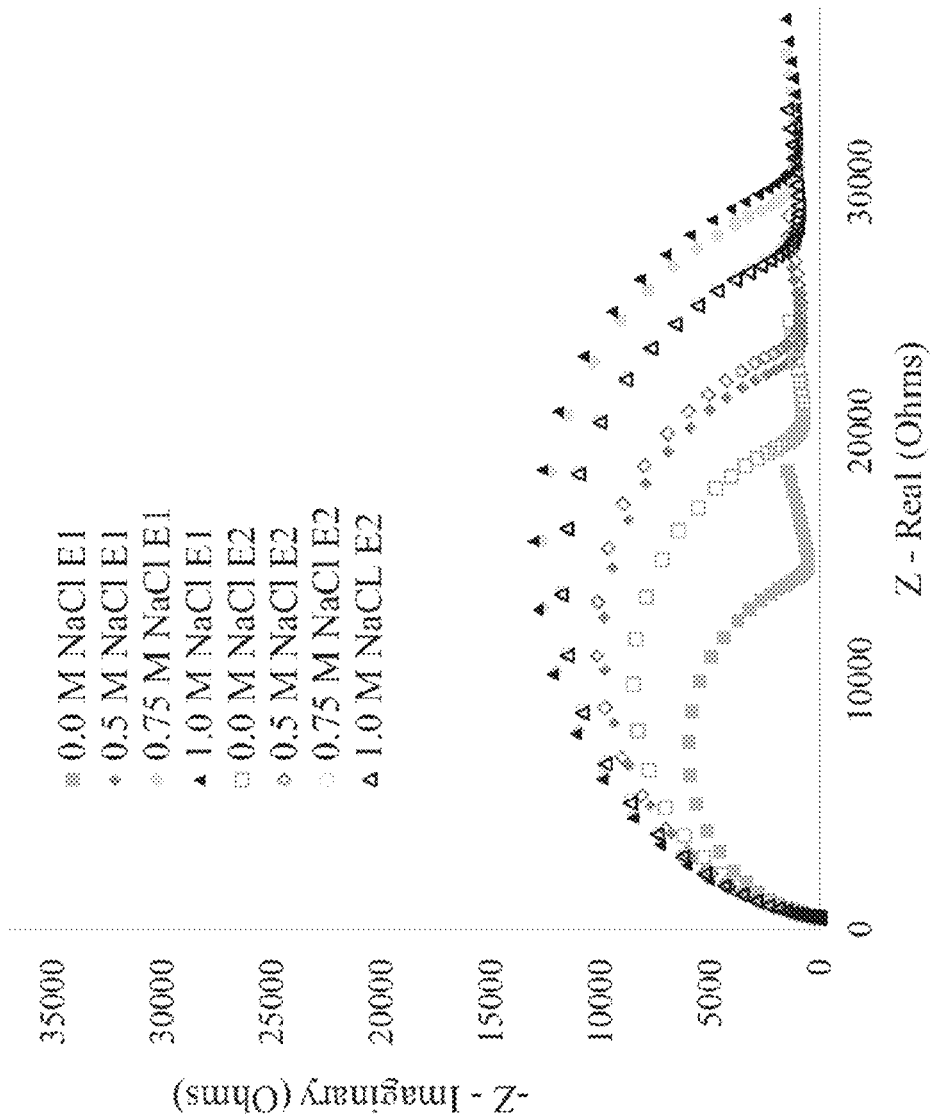
FIG. 25 shows replicate impedance spectra from an I40 modified electrode after exposure to a range of NaCL concentrations from 0.0 M NaCl to 1.0 M NaCl.

Replicate data for the foregoing experiment is included in FIG. 25. Surface-immobilization of i40 constrained the polymer's ability to form intermolecular contacts to bury nonpolar regions of the polymer in response to increased sodium chloride molarity. This in turn necessitated the formation of intramolecular contacts to achieve the same extent of hydrophobic burial. It is hypothesized that this constraint increases the dynamic range and tunability of ELP sensor response.

Example 10

Modification with an Electrochemical Tag

Initial studies were performed in which I40 ELP was modified with a common electrochemical tag, ferrocene. Results demonstrated that after that addition of the ferrocene, the I40 increased in hydrophobicity, which resulted in an irreversible fold/aggregation and lacked a stimulus response.

Additional experiments are done with alternative, more hydrophilic, electrochemical tags, specifically safranin, Leishman's eosine methylene blue, and rhodamine B isothiocynate. These tags are conjugated to the C-terminus through traditional surface modifications. Specifically, Leishman's eosine, methylene blue and rhodamine B isothiocynate are purchased and modified to the surface via standard EDC/hydrazine reaction. Safranin has a free amine that is attached to the surface through traditional EDC/NHS chemistry. Surface conjugation can occur directly on the surface, and the modification is confirmed by an increase in mass with eQCM-D. If needed, these polymers are made free-in-solution and purified through size exclusion columns or dialysis. Cyclic voltammetry and amperometry are common electrochemical techniques that are used to measure faradic response of electrochemically active materials. Cyclic voltammetry applies a triangle voltage waveform and measures the current response. Amperometry measures a current at a constant voltage; about 100 mV above the activation potential of the tag chosen is used. A clear electrochemical faradaic current response is observed for each electrochemical tag; increase in the current at the time of stimulus behavior indicates an ELP collapse response.

Example 11

Applied Electric Field Experiments Tethered to the Surface

Studies are performed in which include applying an electric field to ELP surfaces, with and without the electrochemical tag. These studies are designed to investigate the effect when ELP is tethered to a surface. An applied electric field, from 0 V to 1.6 V vs Ag/AgCl is tested with both EIS and eQCM-D. Under these conditions, whether or not a stimulus response can be generated isothermally is determined. If not, either a salt (osmolarity) stimulus or temperature stimulus is applied and a determination made as to whether there is a change in the transition temperature. If an irreversible structure is discovered, further studies are done using ATR-FTIR and AFM. Controls are important because the applied electric field can influence the double layer capacitance, measured as both a mass and dissipative change in eQCM-D and as an impedance change with EIS. One negative control (a bare electrode) and a positive control is tested. Once deposited, we will confirm a stimulus response via temperature ramping of our analytical system. Additional hydrophobic electrochemical tags are assessed. With these studies: (1) ELPs are electrochemically tagged and assessed and (2) tagged and non-tagged ELPs on 2-dimensional surfaces of the invention are investigated and compared with respect to attachment and stimulus behavior.

Example 12

Creating and Qualifying an ELP-Streptavidin Surface

A 2-dimensional surface can be further modified with an electrochemical tag by adding a lysine (free amine) near the C-terminus of the ELP via mutagenesis. This creates two potential modification sites (i.e. for electrochemical tags and one for a biorecognition element, for example, streptavidin), far from the surface. The free amine is activated with NHS-phosphine surface crosslinker and is bound to streptavidin-hydrazide (SA). Conjugation is confirmed with eQCM-D and ATR-FTIR. The ELP:SA construct is tested to observe shifts in the stimuli response and transition temperatures with eQCM-D and EIS. The response of tagged ELP:SA provides a real-time faradaic signal, which monitors collapse associated with a current response. All four ELPs (SEQ ID NO: 4-7) are modified with SA to optimize the hydrophobicity and length of the ELP length in the sensor design.

Example 13

Biorecognition ELPs

ELP-Surface to Cytokines (IL-1β)

Cytokines are biomarkers that require point-of-need testing. For example, IL-1β and IL-6 are of growing interest because of their impact on cell signaling and significant impact on the immune system and cell behavior. Both have been linked to infectious, autoimmune, and malignant disorders and also potential biomarkers for pain management, depression, schizophrenia, and inflammatory diseases (e.g. arthritis). IL-1β has been linked to opioid use disorder, leading to the opioid epidemic in the USA. Biotinylated IL-1β antibodies (IL1β-Ab) are readily available, and can be conjugated to a surface through traditional SA:biotin interactions.

Studies are performed to confirm the conjugate (ELP:SA: IL1β-Ab) with eQCM-D, ATR-FTIR and AFM, and the transition temperature and stimuli behavior are confirmed via eQCM-D and EIS. After conjugation and confirmation, the stimulus response, via analyte binding, is tested by adding IL-1β to the solution at low quantities on-top of the sensor. If the surface is tuned to elicit a collapse response after IL-1β binding, the collapse response is measured isothermally using eQCM-D and EIS with untagged ELP and using cyclic voltammetry or amperometry with tagged ELP. For tagged ELP, the faradaic response is directly linked to the collapse response (and analyte binding), but untagged ELP is more convoluted as binding of IL-1β, and collapse, can cause similar signals. Therefore, a temperature ramping is done to ensure binding occurs; a shift in the transition temperature is observed in complexed IL-1β to ELP:SA: IL1βAb constructs observed with EIS. Controls are prepared, specifically, ELP:SA exposed to IL-1β (no recognition element), bare electrode exposed to IL-1β (no recognition element), and bare electrode "modified" with IL1β-Ab (no attachment of recognition element to gold surface); all three controls provide no to minimal signal after exposure to IL-1β and temperature ramping.

ELP-Surface to Chemokines (CXCL-10)

Another interesting biomarker, in a similar family to IL-1β is CXCL-10. From the chemokine family, CXCL-10 is also associated with an inflammatory response and can be used as a biomarker for opioid use disorder and other diseases. Similar to the IL-10 experiments (above herein), CXCL10-Ab is attached to the surface via SA:biotin interaction. Also, similar controls, are run. This new sensor is only responsive to CXCL-10 and not IL-1β, because of the change in recognition element. Both this sensor construct, and the IL-1β sensor construct, are tested in the presence of each competitive protein (both IL-1β and CXCL-10).

The constructed and tested ELP surfaces respond to their specific analyte at physiological relevant concentrations, pg/mL to ng/mL. If the surface is at a condition just below the transition temperature, the analyte binding shifts the transition temperature, isothermally causing an ELP stimulus response measured with eQCM-D, EIS, and cyclic voltammetry. Unlike the controls, binding of IL-1β or CXCL-10 to the ELP constructs cause a larger signal and have a different temperature response compared to the controls. Because each individual ELP is isolated on the surface, the quantity of signal correlates to the amount of ELP collapsed, which correlates to the quantity of analyte bound to ELP:SA:antibody construct.

EQUAVALENTS

It is to be understood that the methods and compositions that have been described above are merely illustrative applications of the principles of the invention. Numerous modifications may be made by those skilled in the art without departing from the scope of the invention.

Although the invention has been described in detail for the purpose of illustration, it is understood that such detail is solely for that purpose and variations can be made by those skilled in the art without departing from the spirit and scope of the invention which is defined by the following claims.

The contents of all literature references, publications, patents, and published patent applications cited throughout this application are incorporated herein by reference in their entirety.

TERMS AND ABBREVIATIONS

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the foregoing detailed description and the claims.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that can depend on the desired properties sought and/or limits of detection under standard test conditions/methods.

While the present disclosure has been particularly described in conjunction with specific embodiments, it is evident that many alternatives, modifications, and variations will be apparent to those skilled in the art in light of the foregoing description. It is therefore contemplated that the appended claims will embrace any such alternatives, modifications, and variations as falling within the true spirit and scope of the present disclosure.

What is claimed is:

1. A 2-dimensional metal surface, comprising:
   a plurality of elastin-like polymers (ELPs), each ELP covalently attached to the 2-dimensional metal surface and covalently attached to at least one biorecognition element, wherein the ELPs are configured to transition between at least two conformational states in the absence of in-solution ELPs.

2. The 2-dimensional metal surface of claim 1, wherein the ELPs are configured as part of a monolayer.

3. The 2-dimensional metal surface of claim 1, wherein the biorecognition element is configured to bind at least one bioanalyte.

4. The 2-dimensional metal surface of claim 3, wherein the ELPs are configured to have an altered stimulus response behavior when the biorecognition element is bound to the bioanalyte.

5. The 2-dimensional metal surface of claim 4, wherein the stimulus response behavior is a temperature response behavior.

6. The 2-dimensional metal surface of claim 4, wherein the stimulus response behavior is an ionic strength response behavior.

7. The 2-dimensional metal surface of claim 4, wherein the stimulus response behavior is a pH response behavior.

8. The 2-dimensional metal surface of claim 4, wherein the stimulus response behavior is an electric field response behavior.

9. The 2-dimensional metal surface of claim 1, wherein the ELPs are configured with one or more electrochemical tags.

10. The 2-dimensional metal surface of claim 1, wherein the at least two conformational states comprise an elongated state and a collapsed state of the ELP.

11. The 2-dimensional metal surface of claim 1, wherein the biorecognition element is a protein.

12. The 2-dimensional metal surface of claim 1, wherein the ELPs are configured to transition between the at least two conformational states in response to ligand binding to the biorecognition element.

13. The 2-dimensional metal surface of claim 1, wherein the 2-dimensional metal surface comprises gold.

14. The 2-dimensional metal surface of claim 1, wherein the covalently-attached ELPs are the only ELPs in a system that comprises the 2-dimensional metal surface.

15. The 2-dimensional metal surface of claim 1, wherein the covalently-attached ELPs are end-tethered to the 2-dimensional metal surface.

16. An electrochemical sensor comprising the 2-dimensional metal surface of claim 1.

17. The electrochemical sensor of claim 16, wherein the electrochemical sensor further comprises an electrode.

18. The electrochemical sensor of claim 17, wherein the sensor is configured to have an altered stimulus response behavior that can be detected with an electrochemical detection technique when the biorecognition element is bound to the bioanalyte.

19. A device comprising the 2-dimensional metal surface of claim 1.

20. An electrode comprising the 2-dimensional metal surface of claim 1.

21. A 2-dimensional metal surface, comprising:
   a plurality of elastin-like polymers (ELPs), each ELP covalently attached to a biorecognition element and the 2-dimensional metal surface, wherein the biorecognition element is configured to bind at least one bioanalyte and alter the conformational state of the ELPs based on the binding of the bioanalyte in the absence of in-solution ELPs.

22. The 2-dimensional metal surface of claim 21, wherein the ELPs are configured as part of a monolayer.

23. A method of using a 2-dimensional metal surface capable of performing a stimulus-response interaction, comprising:
   contacting a sample with the 2-dimensional metal surface comprising a plurality of elastin-like polymers (ELPs), each ELP covalently attached to the 2-dimensional metal surface and covalently attached to at least one biorecognition element, wherein the ELPs transition between at least two conformational states in response to the ELPs being contacted with at least one stimulus in the absence of in-solution ELPs; and
   monitoring a state transition of the sample-contacted ELPs using at least one electrochemical detection technique capable of detecting the state transition.

24. The method of claim 23, wherein the monitored state transition of the sample-contacted ELPs is compared to a control state of the ELPs not contacted with the at least one stimulus, and a difference detected between the monitored state transition and the control state indicates the presence of the at least one stimulus in the sample.

* * * * *